US008515143B2

(12) United States Patent
Oonishi et al.

(10) Patent No.: US 8,515,143 B2
(45) Date of Patent: Aug. 20, 2013

(54) EMBRYO QUALITY EVALUATION ASSISTANCE SYSTEM, EMBRYO QUALITY EVALUATION ASSISTANCE APPARATUS AND EMBRYO QUALITY EVALUATION ASSISTANCE METHOD

(75) Inventors: Yasuhito Oonishi, Saitama (JP); Sho Sanami, Tokyo (JP); Kei Imai, Nishigo (JP)

(73) Assignees: Dai Nippon Printing Co., Ltd., Tokyo (JP); National Livestock Breeding Center, Nishigo (JP)

( * ) Notice: Subject to any disclaimer, the term of this patent is extended or adjusted under 35 U.S.C. 154(b) by 568 days.

(21) Appl. No.: 12/654,823

(22) Filed: Jan. 5, 2010

(65) Prior Publication Data
US 2010/0195877 A1    Aug. 5, 2010

(30) Foreign Application Priority Data
Jan. 9, 2009   (JP) .................................. 2009-003785

(51) Int. Cl.
*G06K 9/00*   (2006.01)
(52) U.S. Cl.
USPC ......................................................... 382/128
(58) Field of Classification Search
USPC ......................................................... 382/128
See application file for complete search history.

(56) References Cited

U.S. PATENT DOCUMENTS

| | | | |
|---|---|---|---|
| 7,469,056 B2* | 12/2008 | Ramm et al. | 382/128 |
| 2002/0068358 A1* | 6/2002 | Campbell et al. | 435/289.1 |
| 2008/0247628 A1* | 10/2008 | Ramsing et al. | 382/133 |
| 2010/0103512 A1* | 4/2010 | Ranoux et al. | 359/398 |

FOREIGN PATENT DOCUMENTS
JP    B2-3693907    9/2005

* cited by examiner

Primary Examiner — Gerald J. O'Connor
Assistant Examiner — Trang Nguyen
(74) *Attorney, Agent, or Firm* — Oliff & Berridge, PLC

(57) ABSTRACT

An embryo quality evaluation assistance system including an image pickup unit for picking up an image of the embryo, and a computer that communicates data with the embryo observing apparatus to assist quality evaluation of the embryo. The computer includes a time-series image storing unit that stores a time-series image picked up by the embryo observing apparatus, an embryo image extracting unit that extracts an embryo image from the time-series image, and an active site extracting unit that compares an embryo image based on a first time-series image with an embryo image based on a second time-series image picked up before or after a predetermined time from a pickup time of the first time-series image, and extracts as an active site a set of pixels when the difference between pixel values of corresponding pixels of the first and second time-series images is larger than a predetermined threshold value.

12 Claims, 21 Drawing Sheets

FIG. 21
(a)
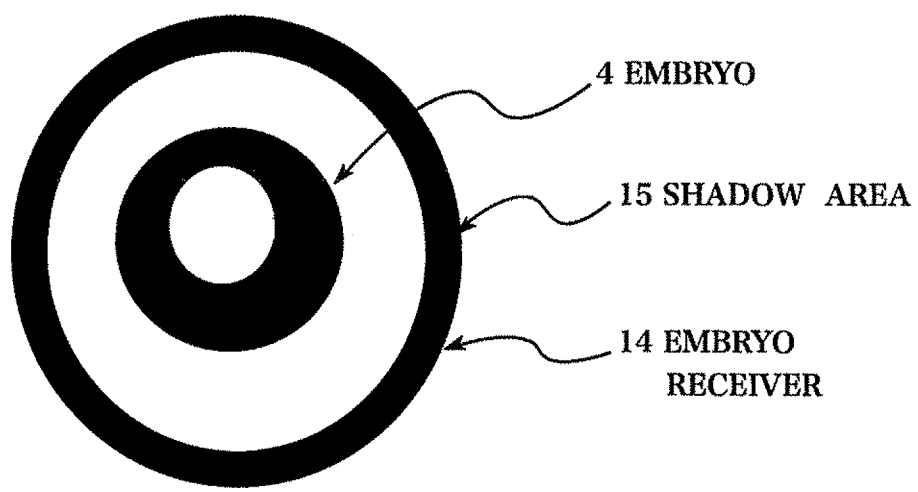
(b)
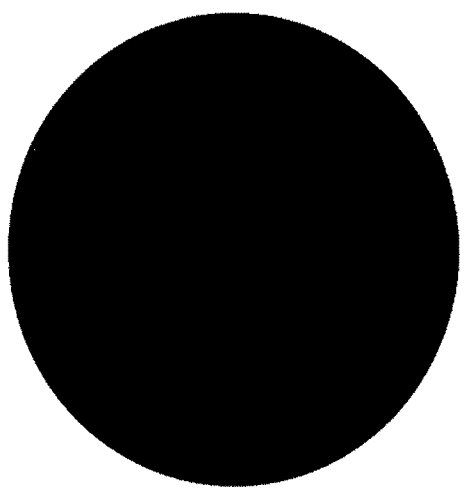

FIG. 26

QUALITY CODE OF EMBRYOS OF CATTLE

| QUALITY CODE | RANK | FEATURE | | | | APPLICATION |
|---|---|---|---|---|---|---|
| | | GROWTH STAGE | DEGENERATED SITE | MORPHOLOGY | ZONA PELLUCIDA | |
| | 1A (Excellent) | NORMAL | NO | SIZE, COLOR TONE, DENSITY AND OUTLOOK OF DIVIDED BLASTOMERE ARE EXCELLENT | NO UNEVENNESS | TRANSPLANT OR FREEZE-PRESERVATION |
| | 1A' (Good) | NORMAL | BELOW 15% | SIZE, COLOR TONE, DENSITY AND OUTLOOK OF DIVIDED BLASTOMERE ARE EXCELLENT | NO UNEVENNESS | TRANSPLANT OR FREEZE-PRESERVATION |
| | 2B (Fair) | NORMAL | BELOW 50% | NO PROBLEM | — | TRANSPLANT OR FREEZE-PRESERVATION |
| | 3C (Poor) | SLIGHTLY DEFECTIVE | BELOW 75% | EACH CELL HAS MANY ABNORMALITIES IN OUTLOOK AND SIZE | — | TRANSPLANT OR FREEZE-PRESERVATION OR DISCARD BASED ON OBSERVATION OF SHAPE AFTER CULTURE |
| | 4D (OUT OF RANK) | DELAY OF GROWTH | ABOVE 76% | DEGENERATED EMBRYO, NON-FERTILIZED EMBRYO | — | DISCARD |

EMBRYO QUALITY EVALUATION ASSISTANCE SYSTEM, EMBRYO QUALITY EVALUATION ASSISTANCE APPARATUS AND EMBRYO QUALITY EVALUATION ASSISTANCE METHOD

BACKGROUND OF THE INVENTION

1. Field of the Invention

The present invention relates to an embryo quality evaluation assistance system that assists quality evaluation of an embryo, etc. The assistance system comprises an embryo observing apparatus having an image pickup unit for picking up an image of an embryo and a computer for transmitting/receiving data to/from the embryo observing apparatus.

2. Description of the Related Art

There is known a technique of culturing embryos of cattle, etc. in an incubator and making these embryos grow until they reach an implantable stage. In the case of in-vitro embryos of cattle, a skilled person takes out the embryos from an incubator on the seventh day from start of the culture and observes these embryos through a microscope to evaluate the final quality of the embryos.

FIG. 26 is a diagram showing quality codes of embryos of cattle. A skilled person observes embryos through a microscope to judge respective features (growth stage, degenerated site, morphology, zona pellucida). Then, the skilled person determines a quality code for each of embryos in accordance with an application. The degenerated site is a site at which cells are abnormal or become extinct.

FIG. 27 is a diagram showing the relationship between elapsed days after fertilization of a cow and growth stages. As shown in FIG. 27, the embryos are passed through cleavage embryos (one-cell embryo→2-cell embryo→4-cell embryo→8-cell embryo), and then become morulas after five to six days elapse from the pregnancy. Thereafter, in the process of compact morula→early blastocyst→blastocyst, raptures in which an embryo expands and contracts occur.

However, it is a great stress for embryos that the embryos are taken out from an incubator and observed. Therefore, there has been proposed a mechanism of evaluating the quality of embryos without taking out the embryos from the incubator (see Japanese Patent No. 3693907).

According to the above patent publication, an embryo is moved so as to be located at the center of the visual field of a microscope by operating a sample holder to measure the size of the embryo and also observe the morphology thereof. An oxygen consumption amount is measured on the basis of the measurement and observation results, thereby evaluating the quality of the embryo.

However, in the above patent, a person is required to operate the sample holder to hold an embryo every image pickup operation. Accordingly, images of an embryo cannot be picked up with time, and thus variation of growth stages cannot be observed.

Furthermore, as another problem, it is difficult to identify the boundary between the cells of a cleavage embryo on the basis of a pick-up image. For example, it is difficult to accurately extract the boundary between the cells by executing even edge enhancement processing. Accordingly, when cells are identified through image processing and quality of an embryo is evaluated on the basis of the feature amount of each cell, it would be impossible to evaluate quality of an embryo with high precision if the above problem is not solved.

Still furthermore, evaluation based on visual observation (check) induces dispersion among evaluators, and thus it is desired to evaluate on the basis of information obtained from only pickup images. Therefore, not only the size of the embryo, but also a lot of quantitative information is required.

At present, a research using information in the growth process such as an arrival time to respective growth stages, an occurrence frequency of raptures and a recovery time from raptures has been done in place of the conventional evaluation method (the method of performing observation and evaluation on the seventh day in the culture by the skilled person). Accordingly, it is very beneficial that information in the growth process as described above can be obtained from only pickup images.

SUMMARY OF THE INVENTION

The present invention has been implemented in view of the foregoing problem, and has an object to provide an embryo quality evaluation assistance system, an embryo quality evaluation assistance apparatus and an embryo quality evaluation assistance method that present information beneficial to quality evaluation of embryos without identifying cells in each embryo on the basis of only images which are picked up without holding the embryos. Particularly, the beneficial information contains information in the growth process such as an arrival time to respective growth stages, an occurrence frequency of raptures and a recovery time from raptures.

In order to attain the above object, according to a first aspect of the present invention, an embryo quality evaluation assistance system for assisting quality evaluation of an embryo, comprises: an embryo observing apparatus having an image pickup unit that picks up an image of the embryo; and a computer that transmits/receives data to/from the embryo observing apparatus, wherein the computer comprises: a time-series image storing unit that stores a time-series image picked up by the embryo observing apparatus; an embryo image extracting unit that extracts an embryo image from the time-series image; and an active site extracting unit that compares an embryo image based on a first time-series image with an embryo image based on a second time-series image picked up before or after a predetermined time from a pickup time of the first time-series image, and extracts as an active site a set of pixels associated with corresponding pixels of the first and second time-series images when the difference between pixel values of the corresponding pixels is larger than a predetermined threshold value.

According to the first aspect, information beneficial to quality evaluation of an embryo can be obtained without identifying cells in the embryo by using images picked up without holding the embryo. Particularly, by extracting the active site, the feature amount which provides a clear difference between a normal embryo and a degenerated embryo can be calculated.

The active site extracting unit may correct rotation of the embryo to extract an active site. Accordingly, an accurate active site can be extracted.

The computer may further comprise a processing result display unit that displays the active site extracted by the active site extracting unit while discriminating the active site from other areas. Accordingly, information beneficial to the quality evaluation of the embryo can be presented to a user.

The computer may further comprise a feature amount calculating unit that calculates the size of the embryo from the embryo image extracted by the embryo image extracting unit and the area of the active site extracted by the active site extracting unit, as a feature amount of the embryo.

Furthermore, the computer may further comprise a feature amount analyzing unit that specifies an arrival time to each growth stage on the basis of a variation amount of the area of the active site calculated by the feature amount calculating unit, and specifies at least one of an occurrence time of raptures, an occurrence frequency of raptures or a recovery time from raptures on the basis of a variation amount of the size of the embryo calculated by the feature amount calculating unit. Accordingly, the information which is more beneficial to the quality evaluation of the embryo can be obtained.

The embryo observing apparatus may pick up plural Z slice images as the time-series image every image pickup time, and the active site extracting unit may compares an embryo image based on a first Z slice image with a fertilized image based on a second Z slice image which is picked up at the same Z position as the first Z slice image before or after a predetermined time from a pickup time of the first Z slice image, thereby extracting active sites at all Z positions. Accordingly, the three-dimensional feature amount of the embryo can be calculated and analyzed.

The embryo observing apparatus may further comprise a culturing container having plural embryo receivers formed therein, the image pickup unit may pick up the time-series image while plural embryos arranged in the culturing container are visually contained in a visual field, and the embryo image extracting unit may extract plural embryo images from the time-series image. Accordingly, even when plural embryos are arranged in the same culturing container, they can be observed without mixing up the embryos.

Furthermore, the embryo image extracting unit may remove a shadow area caused by the embryo receivers to extract the embryo images. Accordingly, the embryo image can be accurately cut out.

The feature amount analyzing unit may determine quality of the embryo on the basis of the feature amount of the embryo calculated by the feature amount calculating unit. Accordingly, the quality evaluation of the embryo can be automatically performed.

The feature amount analyzing unit may determine the quality of the embryo on the basis of a peak occurrence frequency of the area of the active site and an accumulation time for which the area of the active site keeps a value smaller than a predetermined threshold value.

According to a second aspect of the present invention, an embryo quality evaluation assistance apparatus for transmitting/receiving data to/from an embryo observing apparatus having an image pickup unit that picks up an image of an embryo and assists quality evaluation of the embryo, comprises: a time-series image storing unit that stores a time-series image picked up by the embryo observing apparatus; an embryo image extracting unit that extracts an embryo image from the time-series image; and an active site extracting unit that compares an embryo image based on a first time-series image with an embryo image based on a second time-series image picked up before or after a predetermined time from a pickup time of the first time-series image, and extracts as an active site a set of pixels associated with corresponding pixels of the first and second time-series images when the difference between pixel values of the corresponding pixels is larger than a predetermined threshold value.

According to a third aspect of the present invention, an embryo quality evaluation assistance method for assisting quality evaluation of an embryo by an embryo observing apparatus having an image pickup unit for picking up an image of the embryo and a computer for transmitting/receiving data to/from the embryo observing apparatus, comprises; picking up a time-series image by the embryo observing apparatus; extracting an embryo image from the time-series image by the computer; and comparing an embryo image based on a first time-series image with an embryo image based on a second time-series image picked up before or after a predetermined time from a pickup time of the first time-series image, and extracting as an active site a set of pixels associated with corresponding pixels of the first and second time-series images when the difference between pixel values of the corresponding pixels is larger than a predetermined threshold value.

According to the present invention, there can be provided the embryo quality evaluation assistance system, etc. that can present the information beneficial to the quality evaluation of the embryo without identifying cells in the embryo. Particularly, the beneficial information is information during culture such the an arrival time to respective growth stages, the occurrence frequency of raptures and the recovery time from raptures.

BRIEF DESCRIPTION OF THE DRAWINGS

FIG. 19 is a diagram showing the outline of an embryo quality evaluation assistance system 1a;

FIG. 21 is a diagram showing the image processing according to the first embodiment;

FIG. 26 is a diagram showing quality codes of embryos of cattle (embryos of cattle)

DETAILED DESCRIPTION OF THE PREFERRED EMBODIMENTS

Preferred embodiments according to the present invention will be described with reference to the accompanying drawings.

First Embodiment

Figure 1:
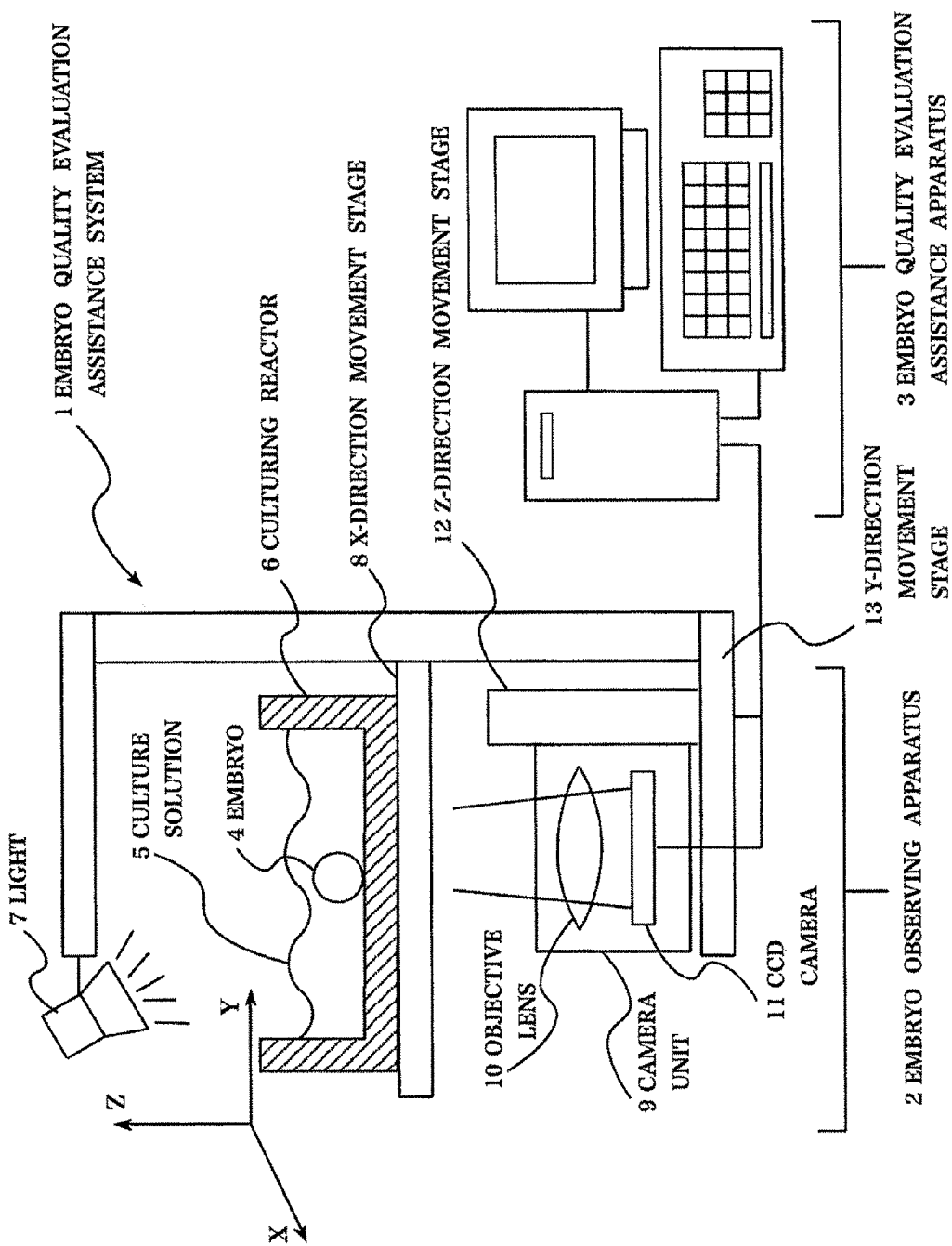
FIG. 1 is a diagram showing the outline of an embryo quality evaluation assistance system 1.

FIG. 1 is a diagram showing the outline of an embryo quality evaluation assistance system 1. As shown in FIG. 1, the embryo quality evaluation assistance system 1 includes an embryo observing apparatus 2 and an embryo quality evaluation assistance apparatus 3. The embryo observing apparatus 2 has a culturing reactor (culturing container) 6 in which an embryo 4 is put and filled with culture solution 5, a light 7 for illuminating the culturing reactor 6, an X-direction movement stage 8 which assists the culturing reactor 6 and on which a transparent glass plate for picking up a transmission image transmitted through the embryo 4 is mounted, a camera unit 9 (image pickup unit), an Z-direction movement stage 12 for moving the camera unit 9 in the up-and-down direction (Z-direction), and an Y-direction movement stage 13 for moving the light 7 and the camera unit 9 in the Y-direction. The camera unit 9 comprises an objective lens 10 and a CCD camera 11. The embryo quality evaluation assistance system 3 is general-purpose computer, for example.

The CCD camera 11 picks up an image of the embryo in the culturing reactor 6 through the objective lens 10. The culturing reactor 6 is moved in the X-direction by the X-direction movement stage 8 and the camera unit 9 is moved in the Y-direction by the Y-direction movement stage 13, whereby the CCD camera 11 can pick up an image at any XY position. The camera unit 9 is moved in the up-and-down direction (Z-direction) by the Z-direction movement stage 12, whereby the CCD camera 11 can pick up a slice image at any Z position.

Figure 2:
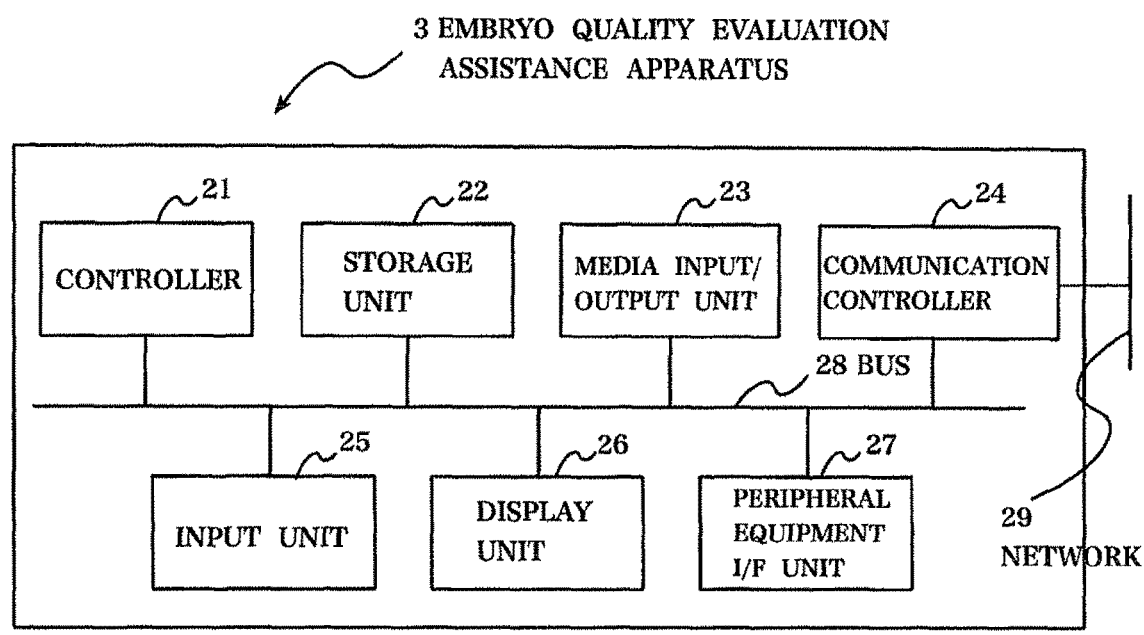
FIG. 2 is a hardware construction of a computer for implementing an embryo quality evaluation assistance apparatus 3.

FIG. 2 is a diagram showing a hardware construction of a computer for implementing the embryo quality evaluation assistance apparatus 3. The hardware construction of FIG. 2 is an example, and various constructions may be adopted in accordance with an application or an object.

The embryo quality evaluation assistance apparatus 3 includes a controller 21, a storage unit 22, a media input/out unit 23, a communication controller 24, an input unit 25, a display unit 26, a peripheral equipment I/F unit 27, etc. which are connected to one another through a bus 28.

The controller 21 comprises CPU (Central Processing Unit), ROM (Read Only Memory), RAM (Random Access Memory), etc.

CPU fetches a program stored in the storage unit 22, ROM, the recording medium or the like into a work memory area on RAM and execute the program to control the operation of each device connected through the bus 28, thereby implementing the processing described later which is executed by the embryo quality evaluation assistance apparatus 3.

ROM is a non-volatile memory, and permanently holds programs such as a boot program, BIOS, etc. of a computer, data, etc.

RAM is a volatile memory, and it has a work area for temporarily storing a program, data or the like which is loaded from the storage unit 22, ROM, the recording medium or the like, and used to execute various kinds of processing by the controller 21.

The storage unit 22 is HDD (hard disk drive), and programs to be executed by the controller 21, data required for executing the programs, OS (Operating System), etc. are stored in HDD. Concerning the programs, the control program corresponding to OS (Operating System), application programs for making the computer execute the processing described later are stored in the storage unit 22.

Each of these program codes is read out by the controller 21 as occasion demands, transferred to RAM, read out by CPU and then executed by various kinds of sections.

The media input/output unit 23 (drive device) inputs/outputs data and has a media input/output device such as CD drive (-ROM, -R, -RW or the like), DVD drive (-ROM, -R, -RW or the like), MO drive or the like, for example.

The communication controller 24 is a communication interface which has a communication control device, a communication port, etc. and through which the computer communicates with a network 29, and it controls the communication with another computer through the network 29.

The input unit 25 inputs data, and has input devices such as a keyboard, a pointing device such as a mouse or the like, numerical keypads, etc.

A manipulation instruction, an operation instruction, data input, etc. can be performed to the computer through the input unit 25.

The display unit 26 has a display device such as a CRT monitor, a liquid crystal panel or the like, and a logical circuit, etc. (video adaptor, etc.) for implementing a vide function of the computer in cooperation with the display device.

The peripheral equipment I/F (interface) unit 27 is a port for connecting the peripheral equipment to the computer, and the computer performs data transmission/reception to/from the peripheral equipment through the peripheral equipment I/F unit 27. The peripheral equipment I/F unit 27 is constructed by USB, IEEE1394, RS-232C or the like, and normally has plural peripheral equipment I/F.

The connection style between the peripheral equipment I/F unit 27 and the peripheral equipment may be a wired style or a wireless style.

The camera unit 9 of the embryo observing apparatus 2 is connected to the embryo quality evaluation assistance apparatus 3 through the peripheral equipment I/F unit 27, and transmits a pickup image to the embryo quality evaluation assistance apparatus 3.

The bus 28 is a passage through which control signals, data signals, etc. are transmitted and received between respective devices.

Figure 3:
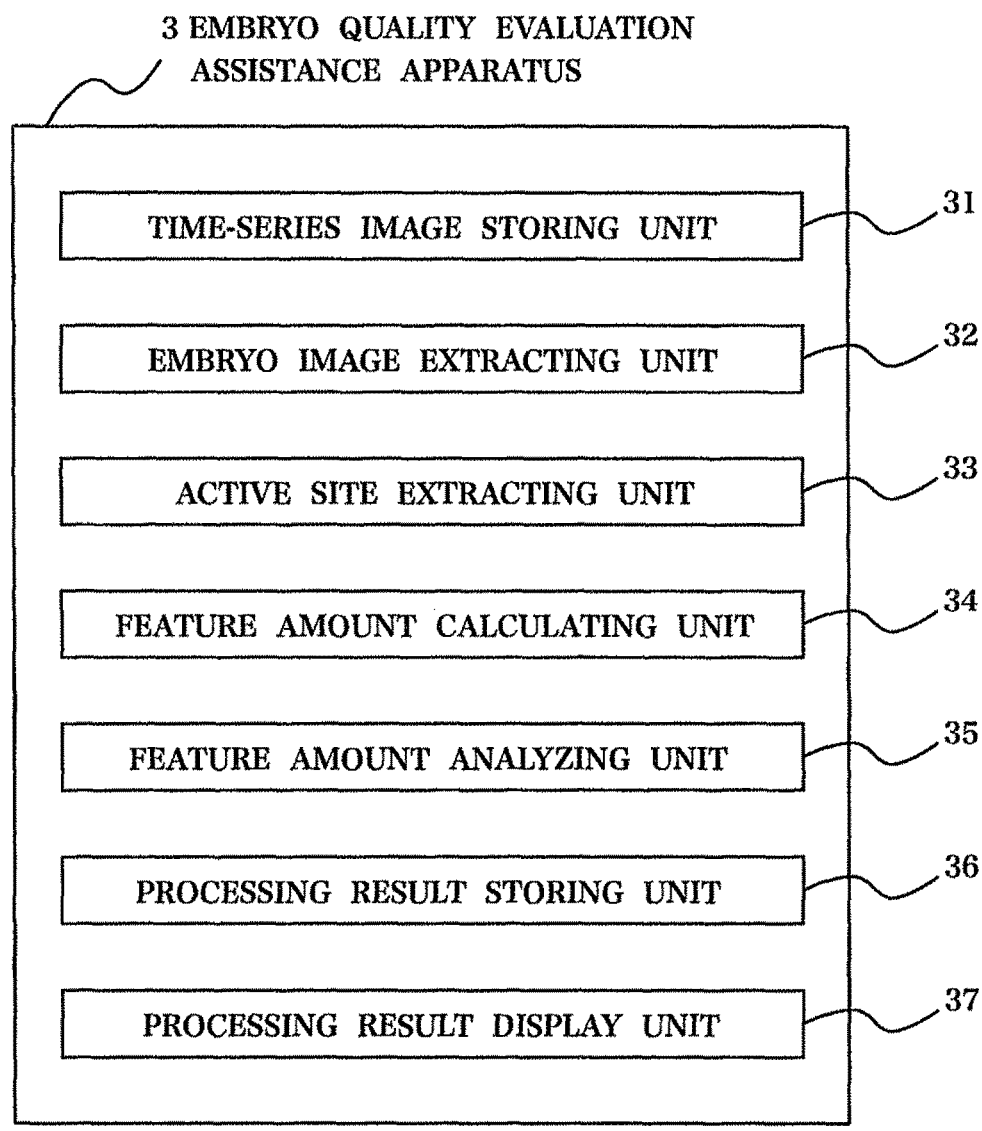
FIG. 3 is a block diagram showing the outline of the function of the embryo quality assistance apparatus 3.

FIG. 3 is a block diagram showing the outline of the embryo quality evaluation assistance apparatus 3. As shown in FIG. 3, the embryo quality evaluation assistance apparatus 3 has a time-series image storing unit 31, an embryo image extracting unit 32, an active site extracting unit 33, a feature amount calculating unit 34, a feature amount analyzing unit 35, a processing result storing unit 36, a processing result display unit 37, etc.

The time-series image storing unit 31 stores an image picked up by the embryo observing apparatus 2. The embryo observing apparatus 2 picks up an image containing the embryo 4 at a fixed interval (for example, at a time interval of 15 minutes). These images are stored as a time-series image (time lapse image) in the time-series image storing unit 31 together with image pickup times.

The embryo image extracting unit 32 extract an embryo image from the time-series image stored in the time-series image storing unit 31. The embryo image is an image obtained by cutting out a minimum approximate circle area containing the embryo 4 from the time-series image.

The active site extracting unit 33 compares two embryo images with each other, and extracts an active site. Specifically, the active site extracting unit 33 compared an embryo image based on any time-series image with an embryo image based on a time-series image before or after a predetermined time from the image pickup time of the former time-series image, and extracts as the active site a set of images in which the difference between the pixel values of the corresponding pixels is larger than a predetermined threshold value. When plural time-series images are visually checked, fat droplets (=black points in images) of normal sites move at all times, and fat droplets of degenerated sites (=sites where cells are abnormal or become extinct) do not move. According to this invention, by paying attention to this phenomenon, the set of pixels whose the difference of pixel values are larger than a predetermined threshold value are extracted as an active site. The variation of the extracted active site is great to the extent that it is determined as a normal site.

Here, the significance of the extraction of the active site will be described.

For example, a feature amount such as an average value or standard deviation of the pixel values of all pixels contained in an embryo image also reflects the pixel values of a site which is not extracted as an active site (non-active sit), and thus it is considered that the difference between a normal embryo and a degenerated embryo is not clear in some cases.

On the other hand, the feature amount based on only the active site can be calculated by extracting the active site as in the case of the present invention. The feature amount based on only the active site does not reflect the pixel value of the non-active site, and thus the difference between the normal embryo and the degenerated embryo is clear. The feature amount as described above makes it easy to identify the normal embryo and the degenerated embryo, and thus it is particularly beneficial information for the quality evaluation of embryos.

As the feature amount of the embryo 4, the feature amount calculating unit 34 calculates the radius of the embryo 4 from the embryo image extracted by the embryo image extracting unit 32, and calculates the area of the active site extracted by the active site extracting unit 33, for example.

The feature amount analyzing unit 35 specifies an arrival time to each growth stage on the basis of the variation amount of the area of the active site calculated by the feature calculating unit 34, and specifies an occurrence time of raptures, an occurrence frequency of raptures and a recovery time from raptures on the basis of the variation amount of the radius of the embryo 4 which is calculated by the feature amount calculating unit 34.

The processing result storing unit 36 stores the processing results of the embryo image extracting unit 32, the active site extracting unit 33, the feature amount calculating unit 34 and the feature amount analyzing unit 35. The processing result of the embryo image extracting unit 32 corresponds to the extracted embryo image. The processing result of the active site extracting unit 33 corresponds to data representing the position of the extracted active site, for example. The processing result of the feature amount calculating unit 34 corresponds to the radius of the embryo 4 and the area of the active site, for example. The processing result of the feature amount analyzing unit 35 corresponds to the arrival time to each growth stage and the occurrence time of raptures, the occurrence frequency of raptures and the recovery time from raptures.

The processing result display unit 37 displays the processing result stored in the processing result storing unit 36 on the display unit 26. Particularly, the processing result display unit 37 displays the active site extracted by the active site extracting unit 33 while discriminating the active site from other areas (for example, by color coding or the like).

Figure 4:
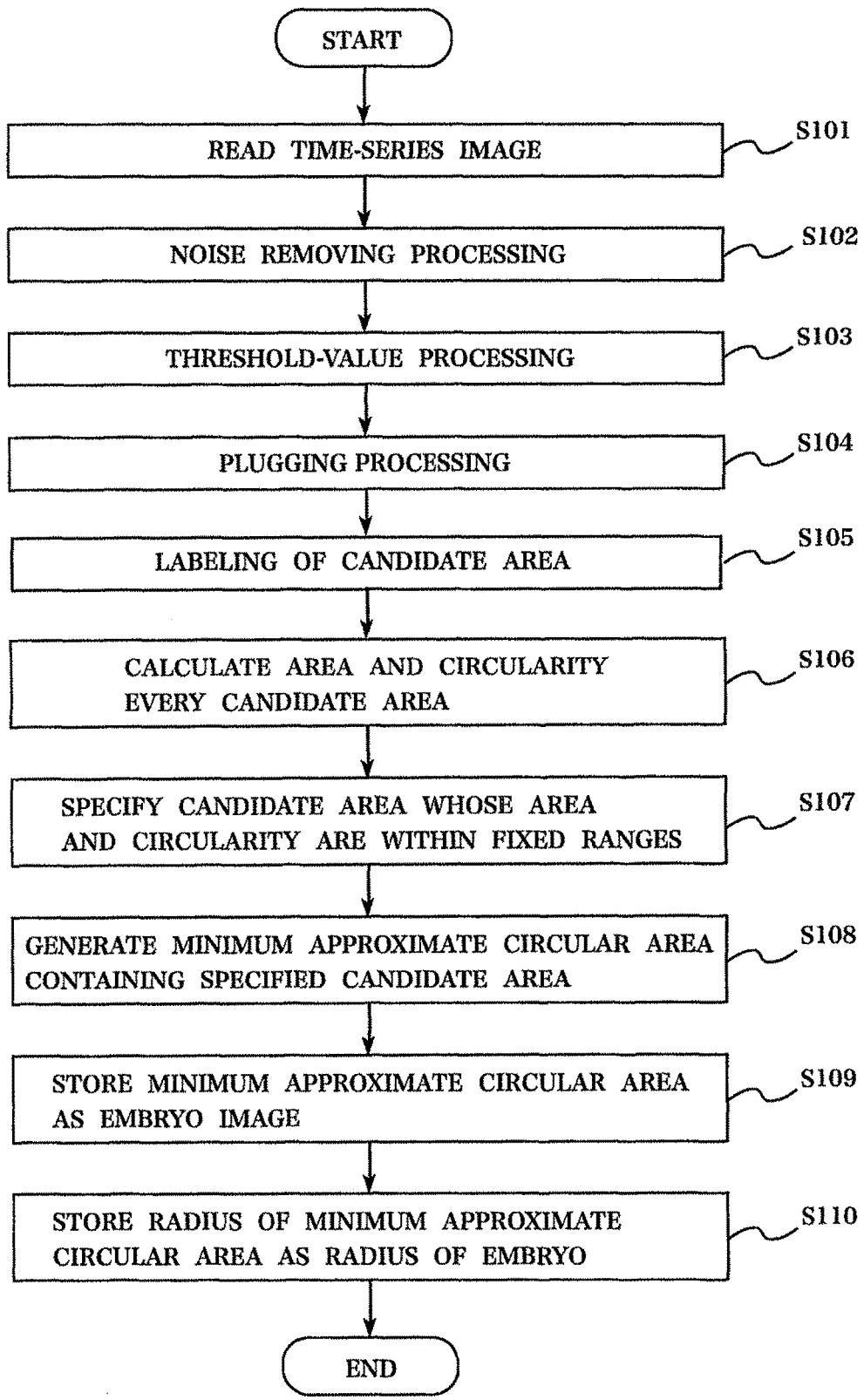
FIG. 4 is a flowchart showing extraction processing of an embryo image in a first embodiment.

FIG. 4 is a flowchart showing the extraction processing of the embryo image in the first embodiment. In the flowchart shown in FIG. 4, the embryo image extracting unit 32 executes the processing of S101 to S108. The processing result storing unit 36 executes the processing of S109, and the feature amount calculating unit 34 and the processing result storing unit 36 execute the processing of S110.

FIGS. 7 to 11 show the processing results obtained by subjecting the pickup image of the embryo of a mouse to the processing of the respective steps of FIG. 4.

The controller 21 of the embryo quality evaluation assistance apparatus 3 reads time-series image stored in the storage unit 22 into RAM (S101). The controller 21 may use the time-series image held in RAM for the following processing before the time-series image is stored in the storage unit 22, that is, just after the image pickup operation.

Figure 7:
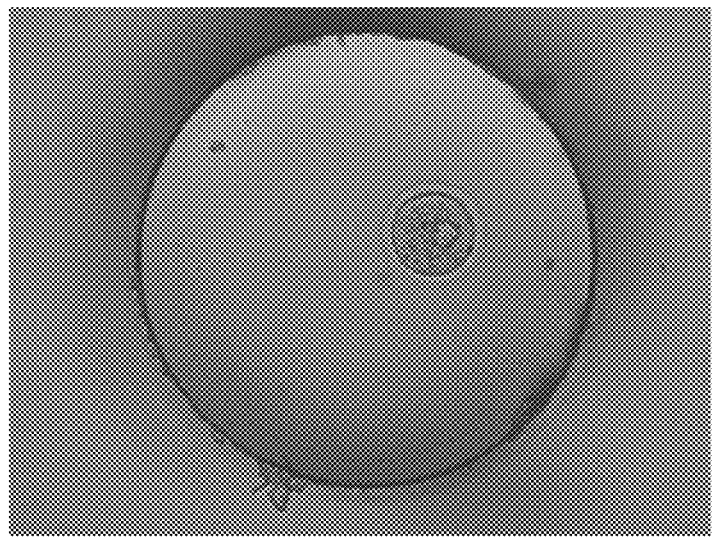
FIG. 7 is a diagram showing an example of a time-series image (an embryo of a mouse)

FIG. 7 is a diagram showing an example of the time-series image. Small circular areas located at the center position and at a slightly right upper position are embryos. According to this invention, information for assisting the quality evaluation of embryos without relying on the visual check is provided. Therefore, the controller 21 executes the processing shown in FIG. 4 to cut out areas of embryos contained in the time-series image read into RAM and extract the areas as embryo images.

Next, the controller 21 executes noise removing processing (S102) and threshold-value processing (S103) on the time-series image read in S101. An average filter method and a median filter method are known as representative methods for the noise removing processing, for example. According to the threshold-value processing, first and second threshold values (first threshold value<second threshold value) are preset, and a pixel value is not less than the first threshold value and also not more than the second threshold value, "1" is set as the pixel value while a pixel value is smaller than the first threshold value or is larger than the second threshold value, "0" is set as the pixel value (=binarization processing). Differential processing for extracting an edge is known as another method.

Figure 8:
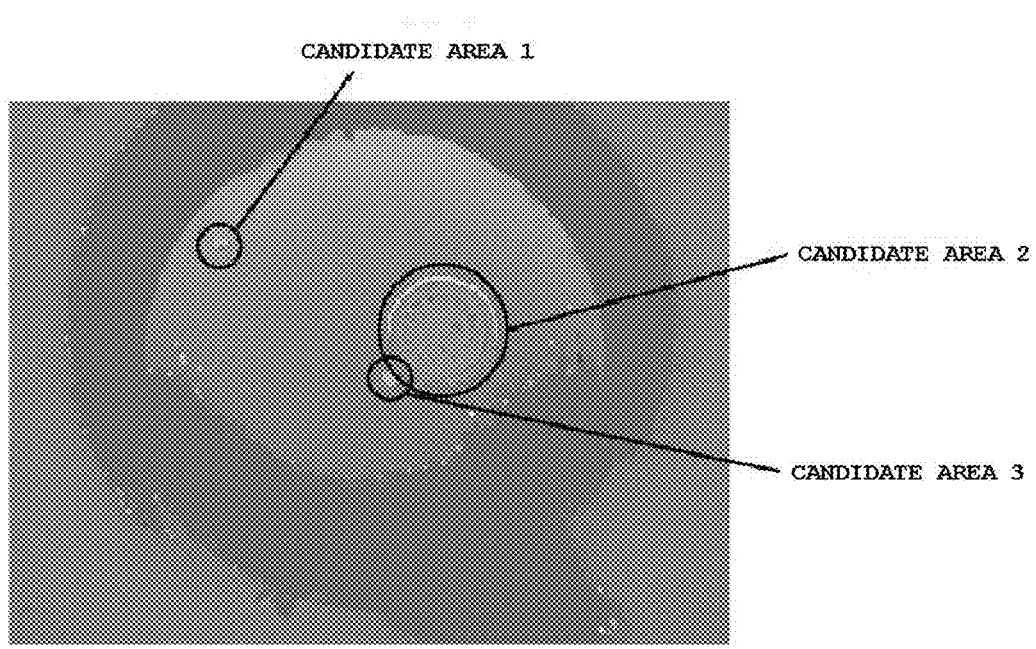
FIG. 8 is a diagram showing an example of an image after threshold-value processing (the embryo of a mouse)

FIG. 8 is a diagram showing an example of the image after the threshold-value processing. By executing the threshold-value processing, objects can be identified as shown in FIG. 8. The identified objects are labeled as a candidate area 1, a candidate 2 and a candidate 3 through the processing of S105 described later.

Next, the controller 21 executes plugging processing (=isolated point removing processing) (S104) on the image after the threshold-value processing in S103. The padding processing is implemented by executing expansion processing at N times and then contraction processing at N times or the like (=closing), for example.

Next, the controller 21 labels the candidate areas (S105). The controller 21 allocates the same number for each set of linked pixels to label each candidate. The assemble of linked pixels is a set of pixels which have the same pixel values and are positionally adjacent to one another.

Next, the controller 21 calculates the area and circularity of each candidate (S106). The area is calculated by counting the number of pixels contained in each candidate area and calculating the product of the number of pixels and the area of one pixel. The circularity is calculated from (4π×area)/(square of peripheral length). The circularity is equal to 1 when the candidate area is a perfect circle, and it approaches to zero as the shape of the candidate area is more complicated. The peripheral length is calculated by scanning the boundary pixels of each candidate and counting the number of sides serving as the boundary.

Next, the controller 21 specifies candidate areas which are within a fixed range in area and circularity (S107). The fixed range is set to the range of values which are permitted with respect to the area and circularity of embryos. In the first embodiment, it is assumed that only one embryo is contained in the time-series image, and thus the number of candidates to be specified is equal to one.

Figure 9:
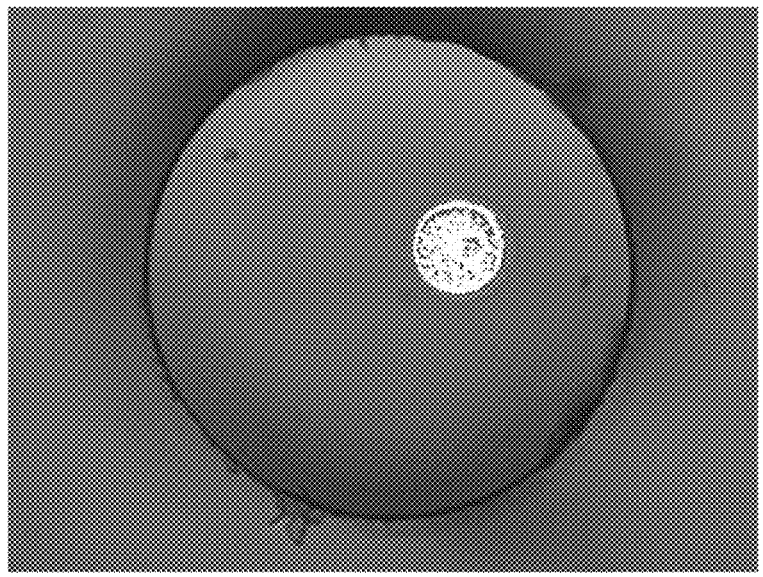
FIG. 9 is a diagram showing a specified candidate area (the embryo of a mouse)

FIG. 9 is a diagram showing a specified candidate. In FIG. 9, the specified candidate is represented by white color. It is apparent that the area of the embryo located at the center and slightly right upper positions (=the area where the candidate area 2 shown in FIG. 8 is plugged) is specified.

Next, the controller 21 generates a minimum approximate circular area containing the specified candidate area (S108). Since the candidate area is not a perfect circle, the length of the longest line segment out of line segments connecting the respective points on the boundary of the candidate area is set to the radius of the minimum approximate circular area.

Figure 10:
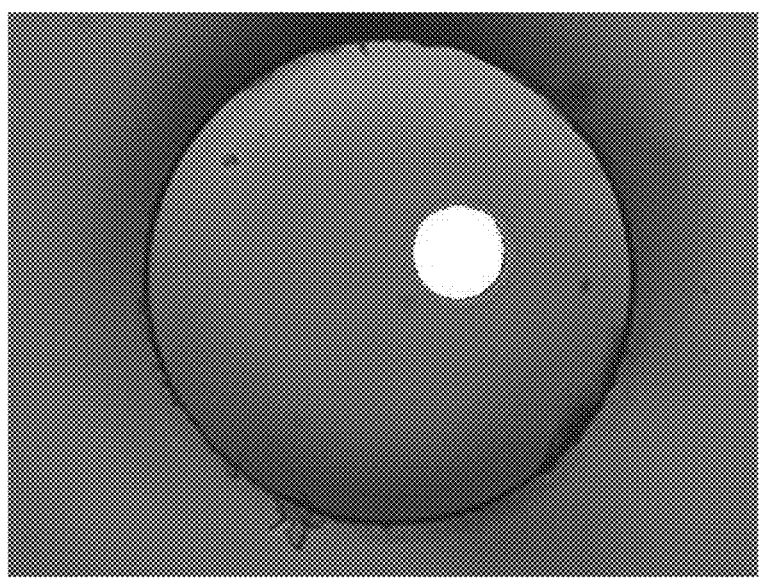
FIG. 10 is a diagram showing a minimum approximate circle area (the embryo of a mouse)

FIG. 10 is a diagram showing the minimum approximate circular area. In FIG. 10, the minimum approximate circular area is represented by white color. It is apparent that the minimum approximate circular area containing the candidate area shown in FIG. 9 is generated.

When the embryo has a shape nearer to an ellipse than a perfect circle, the controller 21 may generate a minimum approximate ellipse area in place of the minimum approximate circular area. In this case, the controller 21 sets the length of the longest line segment out of line segments connecting respective points on the boundary of the candidate as the major axis, and sets the line segment perpendicular to the major axis as the minor axis.

Next, the controller 21 cuts out the minimum approximate circular area as an embryo image and stores it (S109). Furthermore, the controller 21 stores the radius of the minimum approximate circular area as the radius of the embryo (S110).

Figure 11:
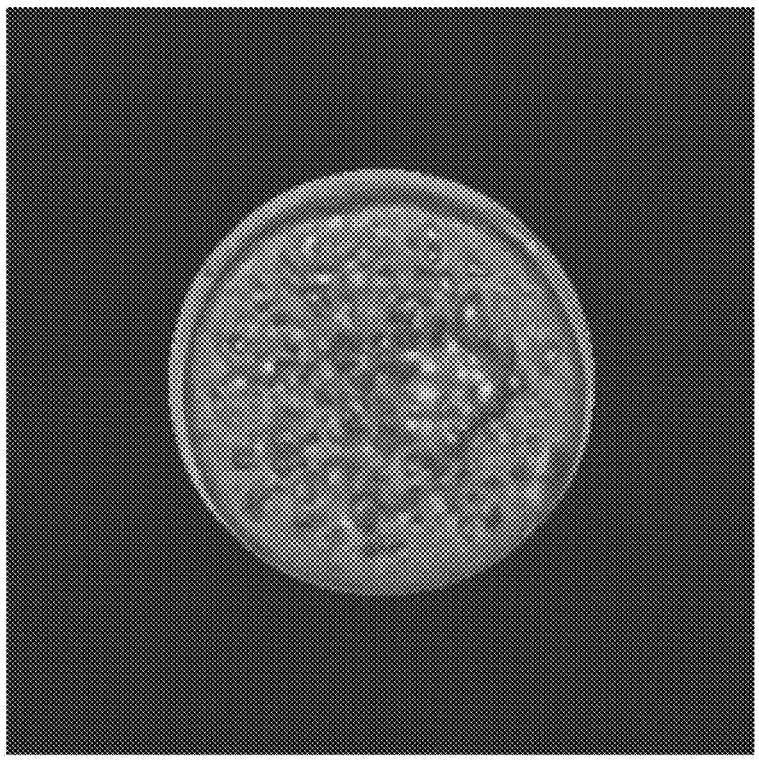
FIG. 11 is a diagram showing an embryo image (the embryo of a mouse)

FIG. 11 is a diagram showing the embryo image. The embryo image of FIG. 11 is obtained by cutting out the pixels corresponding to the minimum approximate circular area from the time-series image of FIG. 7 and enlarging the cut-out image. Through the above processing, the controller 21 extracts the embryo image.

Figure 5:
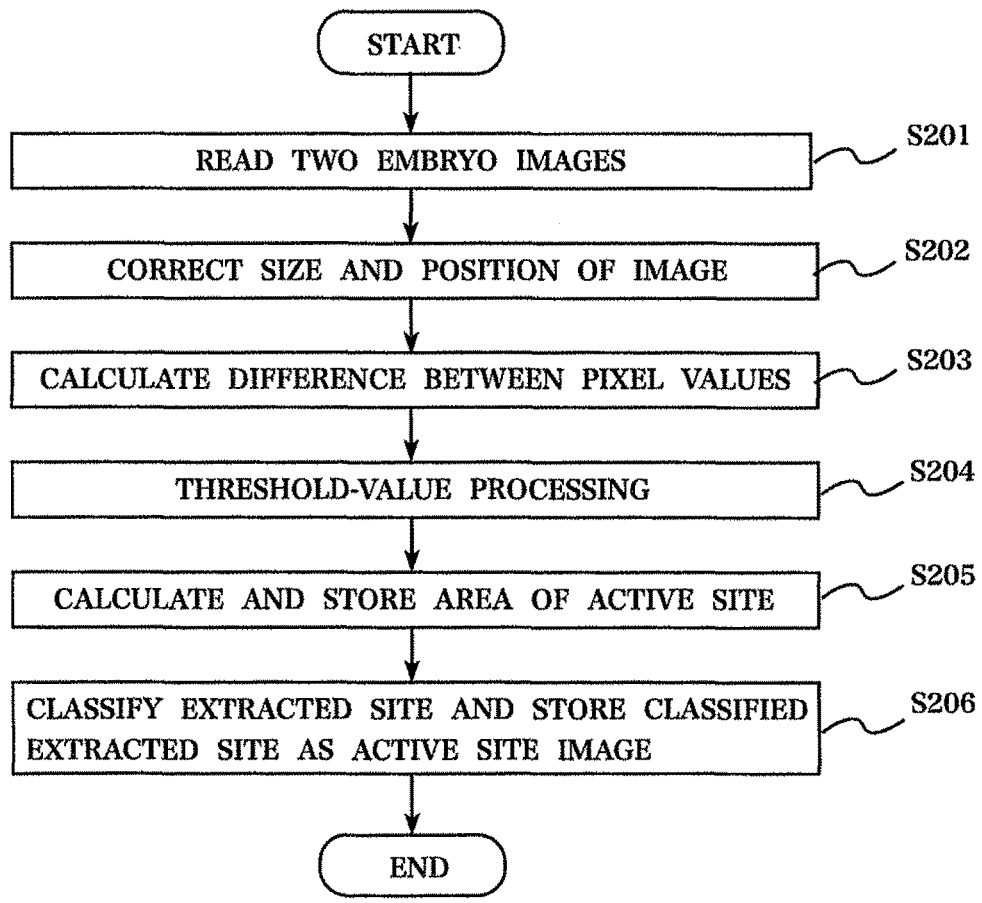
FIG. 5 is a flowchart showing the extraction processing of an active site.

FIG. 5 is a flowchart showing the extraction processing of an active site. In the flowchart of FIG. 5, the active site extracting unit 33 executes the processing of S201 to S204. Furthermore, the feature amount calculating unit 34 executes the processing of S205. The processing result storing unit 36 executes the processing of S205 and S206.

FIGS. 12 to 16 show the processing results obtained by subjecting the processing of each step of FIG. 5 to two embryo images (embryo images of a mouse) which are obtained by the extraction processing of the embryo shown in FIG. 4.

The controller 21 of the embryo quality evaluation assistance apparatus 3 reads two embryo images stored in the storage unit 22 into RAM (S201).

Figure 12:
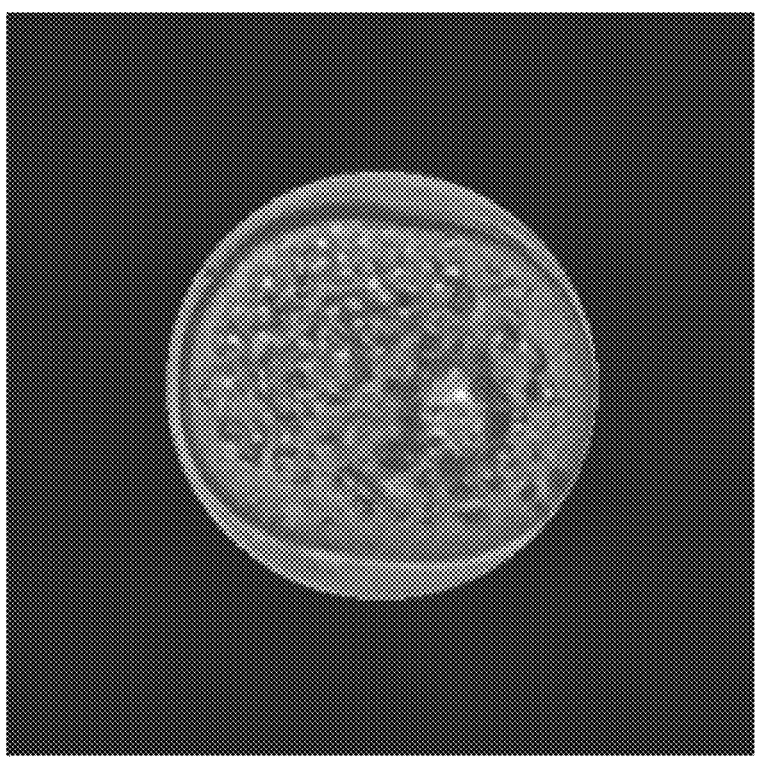
FIG. 12 is a diagram showing an example of an embryo image (the embryo of a mouse)
Figure 13:
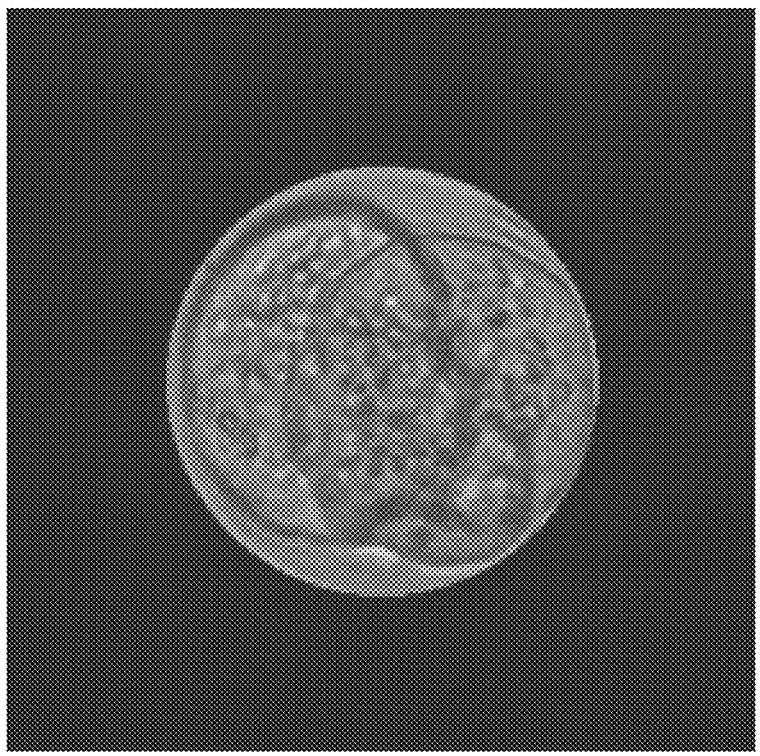
FIG. 13 is a diagram showing an example of an embryo image (the embryo of a mouse)

FIGS. 12 and 13 are diagrams showing examples of embryo images. The embryo image shown in FIG. 13 corresponds to an image picked up after a predetermined time elapses with respect to the embryo image shown in FIG. 12. In detail, FIG. 12 shows an image representing an embryo before cleavage (two-cell cleavage), and FIG. 13 shows an image representing the embryo after the cleavage (two-cell cleavage).

Subsequently, the controller 21 corrects the size, position of the images as pre-processing for the comparison between the two embryo images (S202).

With respect to time-series image of an embryo which is picked up without holding the embryo, when some embryo image is compared with an embryo image before or after a predetermined elapses from the image pickup of the former embryo image, the following variations may be considered as the variation of the overall embryo appearing as an image except for the inner variation of the embryo: (1) the variation in size of the embryo, (2) the positional movement of the embryo and (3) the rotation of the embryo. In order to execute accurate comparison processing, it is necessary to correct the size and position of one of the embryo images.

(1) Concerning the variation of the size of the embryo, for example, the ratio in diameter between both the embryo images is calculated and one of the embryo image may be magnified or reduced. (2) Concerning the positional movement of the embryo, after magnification or reduction, the position of the center of gravity may be made coincident between both the embryo images. (3) Concerning the rotation of the embryo, the processing of correcting the rotation of the embryo will be described with reference to FIG. 6.

Figure 6:
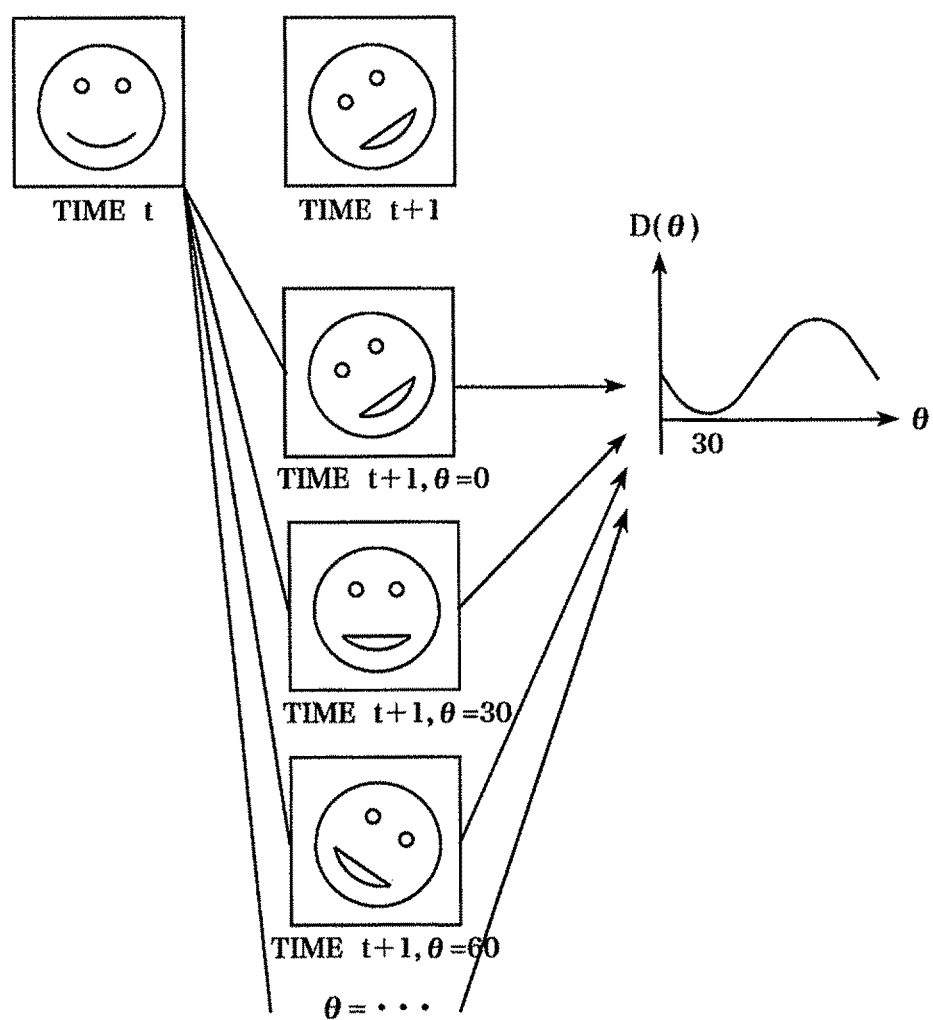
FIG. 6 is a diagram showing the processing of correcting rotation of an embryo.

FIG. 6 is a diagram showing the processing of correcting the rotation of the embryo. In the example shown in FIG. 6, with respect to a first embryo image cut out from time-series image at a time t and a second embryo image cut out from time-series image at a time of t+1, the position of the second fertilized image is corrected so as to be coincident with the first embryo image.

The controller 21 of the embryo quality evaluation assistance apparatus 3 compares the first embryo image with images obtained by rotating the second fertilized image at an angle of θ (θ=0°, 30°, 60°, . . . ), and calculates the difference D(θ) between the images according to the following expression.

$$D(\theta) = \sum_{y} \sum_{x} (R(x, y) - R'(x, y, \theta))^2 \quad (1)$$

Here, R(x,y) represents the pixel value (=brightness value) of a pixel at a position (x,y) of the first embryo image, R'(x,y,θ) represents the pixel value (=brightness value) of a pixel at a position (x,y) of an image obtained by rotating the second embryo image at θ. In the case of a color image, hue, color saturation, luminosity or the like of each pixel may be used in place of the brightness value.

The controller 21 sets the minimum value $\theta_{min}$ of the difference D(θ) between pixels as a rotational amount in the second embryo image with respect to the first embryo image, and the image having the minimum $\theta_{min}$ of the difference D(θ) between pixels is used in the processing of S203 shown in FIG. 5.

Returning to FIG. 5, the controller 21 calculates the difference between the pixel values of the two embryo images (S203). The calculation of the difference between the pixel values in S203 is performed for the purpose of comparing the two embryo images and extracting a site at which variation is great. Therefore, in the case of a grayscale image whose pixel values have gradations from 0 to 255, for example, the difference between pixel values is defined as Diff(x,y)=R(x,y)–

R'(x,y)+127. However, when Diff (x,y) is smaller than 0, Diff (x,y) is set to zero. When Diff (x,y) is larger than 255, Diff (x,y) is set to 255. By defining the difference between pixels as described above, Diff (x,y) is equal to a value around 127 for a portion whose variation is small, also Diff (x,y) is equal to a value near to zero or 255 for a portion whose variation is great.

Figure 14:
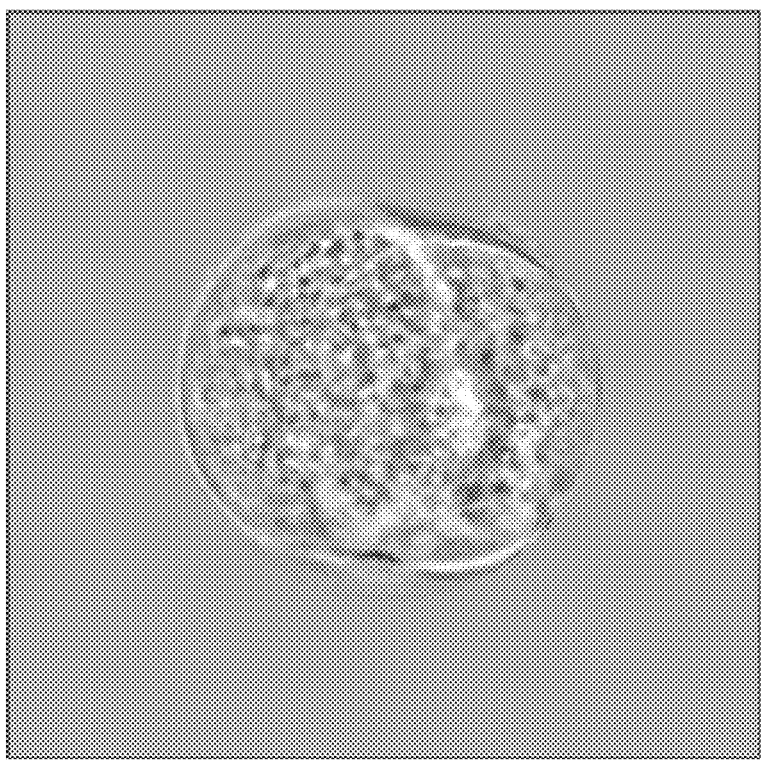
FIG. 14 is a diagram showing a differential calculation result (the embryo of a mouse)

FIG. 14 is a diagram showing the calculation result of the difference. In FIG. 14, a gray portion (intermediate gradation portion) corresponds to a variation-small portion, and a white or black portion corresponds to a variation-great portion.

Next, the controller 21 executes the threshold-value processing (S204). In the threshold-value processing, on the basis of preset first and second threshold values (first threshold value<second threshold value), when a pixel value is not less than the first threshold value and also is not more than the second threshold value (=when variation is small), the pixel value is set to zero. When a pixel value is smaller than the first threshold value or larger than the second threshold value (=when variation is large), the pixel value is set to 1. Here, a set of pixels whose pixel values are set to 1 corresponds to an active site.

Figure 15:
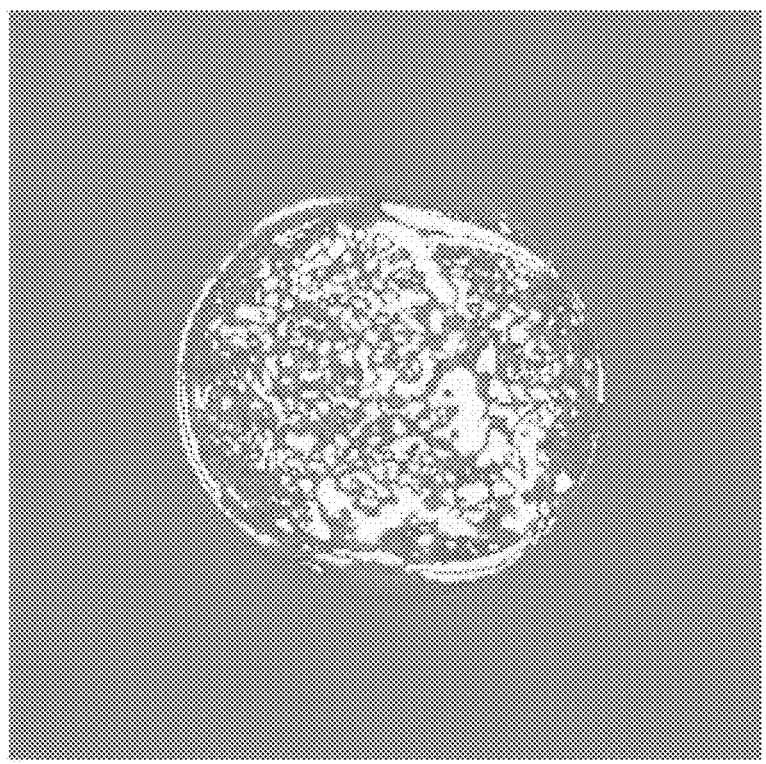
FIG. 15 is a diagram showing a threshold-value processing result (the embryo of a mouse)

FIG. 15 is a diagram showing a result of the threshold-value processing. In FIG. 15, pixels whose pixel values are set to 1 in S204 are represented by white color.

Subsequently, the controller 21 calculates and stores the area of the active site (S205). The area of the active site is calculated by counting the pixels whose pixel values are set to 1 in S204 and calculating the product between the count number of pixels and the area of one pixel.

Next, the controller 21 classifies (colors) the pixels corresponding to the extracted active site with respect to the embryo image read in S201, and stores the classified (colored) pixels as an active site image (S206).

Figure 16:
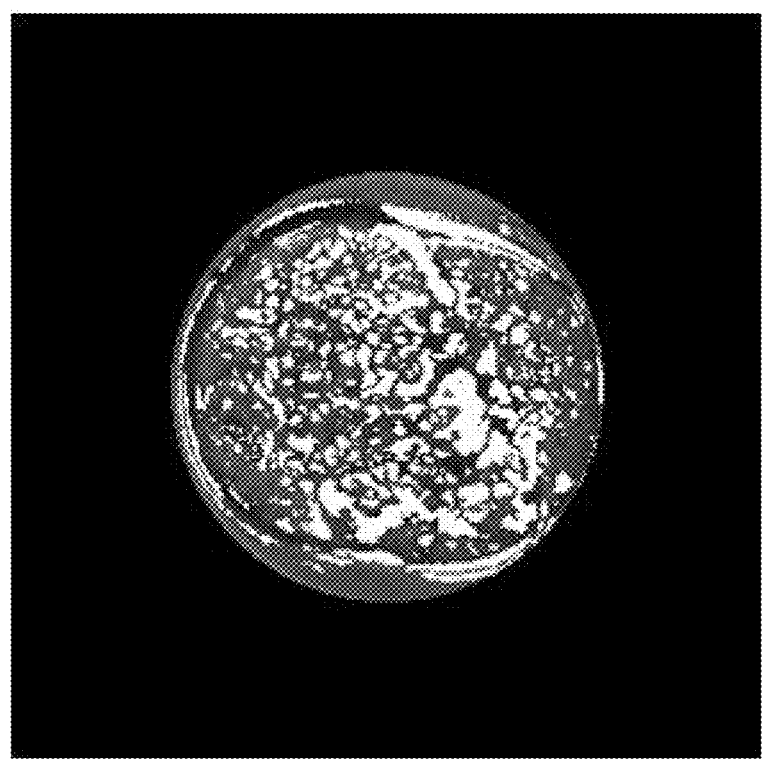
FIG. 16 is a diagram showing an example of an active site image (the embryo of a mouse)

FIG. 16 is a diagram showing an example of the active site image. In FIG. 16, the active site is represented by white color. It is apparent from FIG. 16 that a broad area is extracted as the active site. Through the above processing, the controller 21 extracts the active site.

Figure 17:
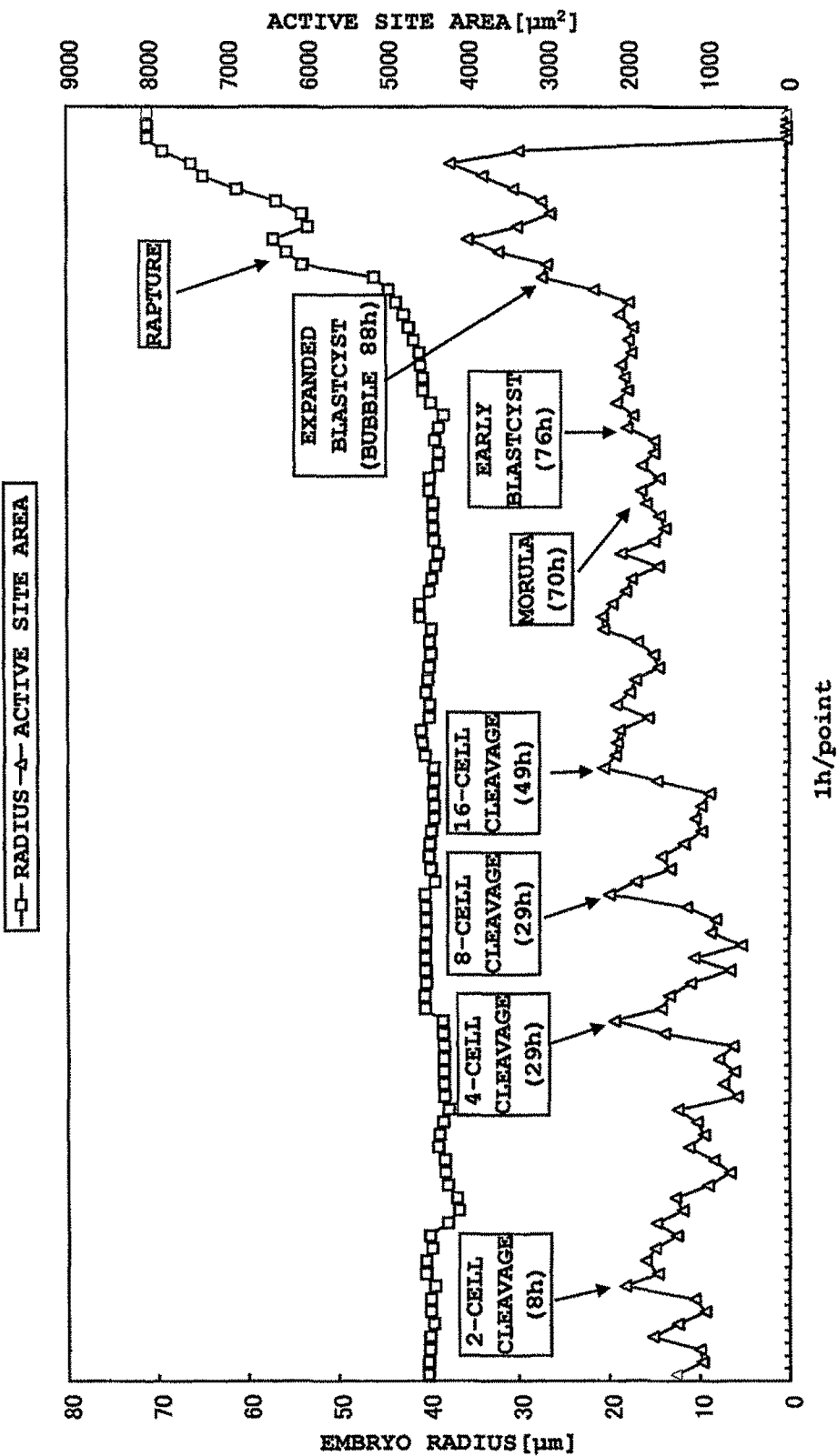
FIG. 17 is a graph of a feature amount concerning a normal embryo (the embryo of a mouse)
Figure 18:
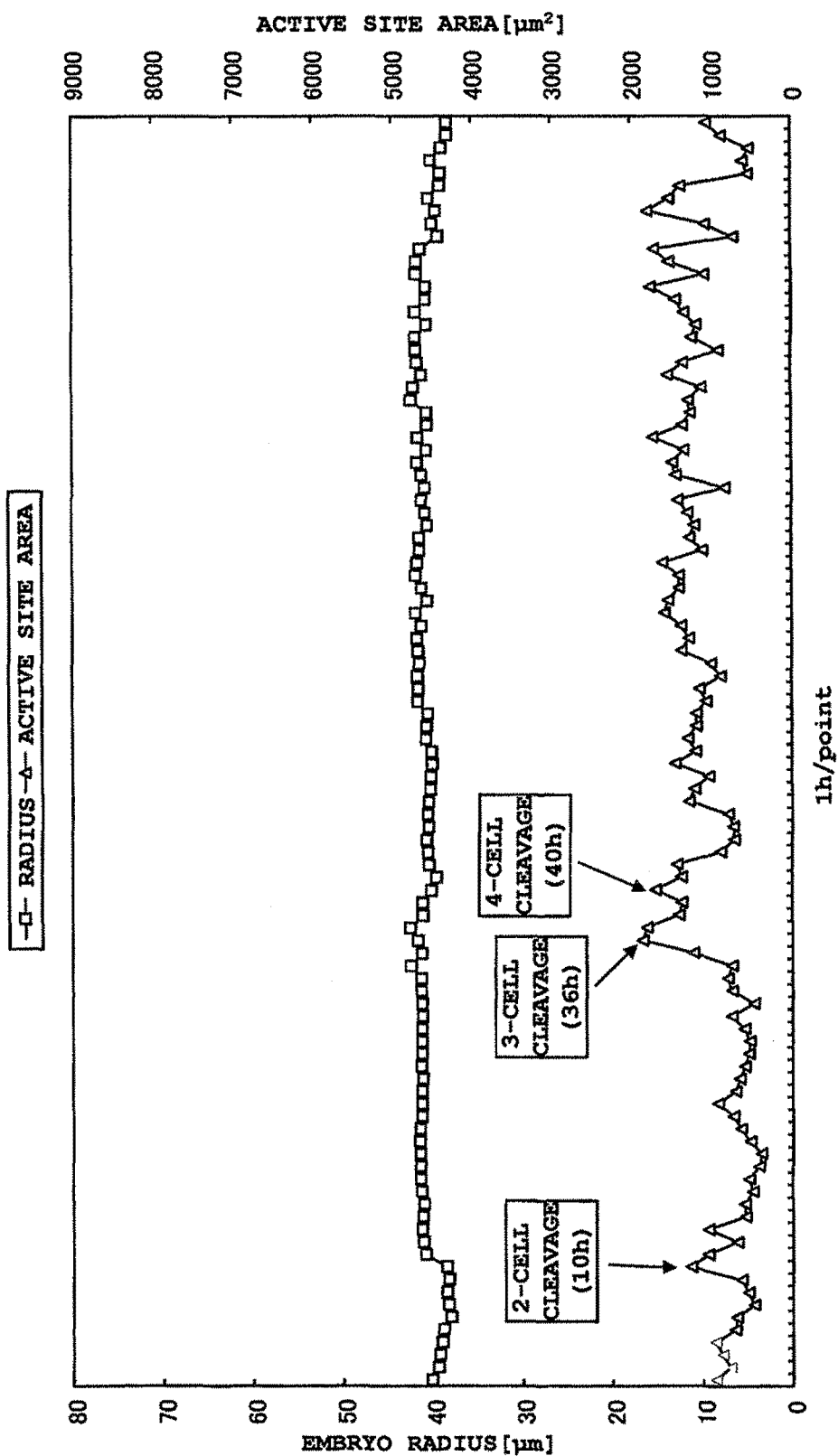
FIG. 18 is a graph of a feature amount concerning a degenerated embryo (the embryo of a mouse)

FIG. 17 is a feature amount graph concerning a normal embryo of a mouse. FIG. 18 is a feature amount graph concerning a degenerated embryo (degenerated embryo) of a mouse. FIGS. 17 and 18 show time-series data of the embryo radius and the active site area stored in the processing result storing unit 36 which are displayed on the display unit 26 by the processing result display unit 37.

In FIGS. 17 and 18, the embryo radius is plotted with rectangles, and the active site area is plotted with triangles. Two-cell cleavage (8 h), 4-cell cleavage (29 h), etc. represent the growth stage of the embryo and the lapse time from an observation start time. For example, it is visually checked for the embryo of the normal embryo shown in FIG. 17 that the embryo reaches the growth stage of 2-cell cleavage after 8 h. The other growth stages and the other lapse times from the observation start time are likewise checked visually. In the following description, the processing of the feature amount analyzing unit 35 based on the knowledge obtained through the visual check will be described.

Referring to FIGS. 17 and 18, it is apparent that before and after cell division such as 2-cell cleavage, 4-cell cleavage, 8-cell cleavage and 16-cell cleavage of FIG. 17 and 2-cell cleavage, 3-cell cleavage and 4-cell cleavage of FIG. 18 is executed, the active site area greatly increases as compared with the active site area just before. On the basis of this knowledge, the feature amount analyzing unit 35 determines that the embryo successively reaches the growth stages such as 2-cell cleavage, 4-cell cleavage, 8-cell cleavage and 16-cell cleavage in this order.

Referring to FIG. 17, it is apparent that when the embryo reaches the growth stage of expanded blastocyst, the active site area and the radius of the embryo increases greatly. On the basis of this knowledge, the feature amount analyzing unit 35 determines that the embryo reaches the growth stage of expanded blastocyst when the increase of the active site area and the increase of the embryo radius exceed predetermined threshold values after a fixed time elapses from the growth stage of cleavage division.

Referring to FIG. 17, it is apparent that the radius of the embryo temporarily decreases and then increases before and after occurrence of rapture. On the basis of this knowledge, the feature amount analyzing unit 35 determines as the occurrence time of rapture a time just before the embryo radius decreases after the embryo reaches the growth stage of the expanded blastocyst, for example. Furthermore, the feature amount analyzing unit 35 determines as the occurrence frequency of rapture a frequency at which the embryo radius decreases after the embryo reaches the growth stage of the expanded blastocyst. Still furthermore, the feature amount analyzing unit 35 determined as the recovery time from rapture a time period from the occurrence time of the rapture till the time when the radius of the embryo returns to the radius of the embryo at the occurrence time of the rapture.

As described above, the feature amounts are analyzed by the feature amount analyzing unit 35, whereby the information concerning the arrival time of the growth stage, the occurrence time of rapture, the occurrence frequency of rapture, the recovery time of rapture, etc. can be obtained by calculation without relaying on the visual check, and displayed on the display unit 26 by the processing result display unit 37.

As described above, according to the first embodiment of the present invention, the embryo quality evaluation assistance system 1 comprises the embryo observing apparatus 2 and the embryo quality evaluation assistance apparatus 3. The embryo quality evaluation assistance apparatus 3 comprises the time-series image storing unit 31 for storing images picked up by the embryo observing apparatus 2, the embryo image extracting unit 32 for extracting an embryo image from the time-series image stored in the time-series image storing unit 31, the active site extracting unit 33 for comparing two embryo images and extracting an active site, the feature amount calculating unit 34 for calculating the feature amount of an embryo, the feature amount analyzing unit 35 for analyzing the feature amount of the embryo, the processing result storing unit 36 for storing the processing result, the processing result display unit 37 for displaying the processing result, etc.

According to the first embodiment, the information beneficial to the quality evaluation of an embryo can be presented without identifying any cell in the embryo by using images which are picked up without holding the embryo.

In the first embodiment, the various kinds of processing are executed by using only a time-series image Z slice image) at one Z position every image pickup time. However, as another embodiment, plural Z slice images may be used every image pickup time.

In this case, the embryo observing apparatus 2 picks up plural Z slice images as the time-series image every image pickup time. The embryo image extracting unit 32 extracts embryo images from all the Z slice images. The active site extracting unit 33 compares an embryo image associated with any Z slice image with an embryo image associated with a Z slice image at the same Z position before or after a predetermined time from the image pickup time of any time-series image every Z position, thereby extracting active sites at all Z positions.

Accordingly, a three-dimensional feature amount can be calculated and analyzed. For example, the feature amount calculating unit 34 calculates the radiuses of the minimum approximate circles from the embryo images extracted by the embryo image extracting unit 32 for all the Z slice images at the same image pickup time, and sets the maximum radius value as the radius of the embryo at the image pickup time concerned. Furthermore, for example, the feature amount calculating unit 34 calculates the total of the areas of the active sites extracted by the active site extracting unit 33 with respect to all the Z slice images at the same image pickup time. Then, the feature amount analyzing unit 35 analyzes the embryo on the basis of the calculated radius of the embryo and the calculated total area of the active sites.

In the forgoing description, the feature amount calculating unit 34 calculates the radius of the embryo as the feature amount which represents the size of the embryo 4, however, the present invention is not limited to this style. For example, the feature amount representing the size of the embryo 4 may be the area, volume or the like of the embryo 4. The area of the embryo 4 is determined by counting the number of pixels contained in the minimum approximate circle and calculating the product of the counted number of pixels and the area of one pixel. The volume of the embryo 4 is determined by calculating the area of the minimum approximate circle from each Z slice image and totalizing the areas of the respective minimum approximate circles.

Second Embodiment

Next, a second embodiment will be described. In the second embodiment, plural embryos are cultured, and time-series images are picked up while the plural embryos are visually contained in a visual field.

The same elements as described in the first embodiment are represented by the same reference numerals, and the description thereof is omitted.

Figure 19:
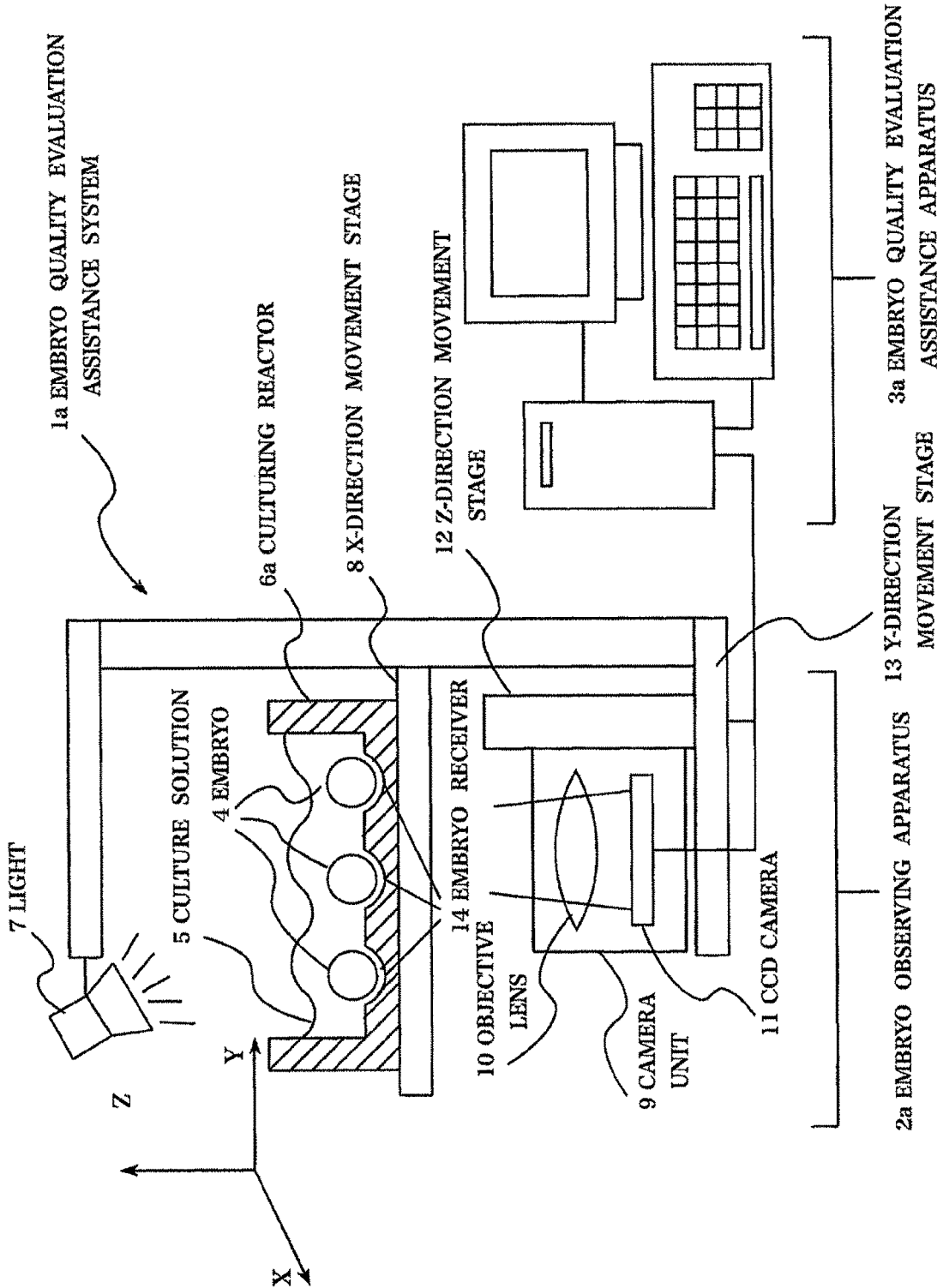

FIG. 19 is a diagram showing the outline of an embryo quality evaluation assistance system 1a. As shown in FIG. 19, the embryo quality evaluation assistance system 1a comprises an embryo observing apparatus 2a and an embryo quality evaluation assistance apparatus 3a.

The embryo observing apparatus 2a includes a culturing reactor (culturing container) 6a containing plural embryos 4, a light 7, an X-direction movement stage 8, a camera unit 9 (image pickup unit), a Z-direction movement stage 12 and a Y-direction movement stage 13. The embryo quality evaluation assistance apparatus 3a is a general-purpose computer, for example.

The culturing reactor 6a has plural embryo receivers 14. The embryo receivers 14 are formed as cylindrical or semispherical dimples on the bottom surface of the culturing reactor 6a. One embryo 4 is disposed in one embryo receiver 14. The embryos 4 are disposed in the embryo receivers 14, whereby the embryos 4 hardly move positionally during culture. When viewed in the vertical direction (Z direction), the area of the embryo receiver 14 is set to be smaller than the area of the embryo 4 at the stage that the culture is finished.

Figure 20:
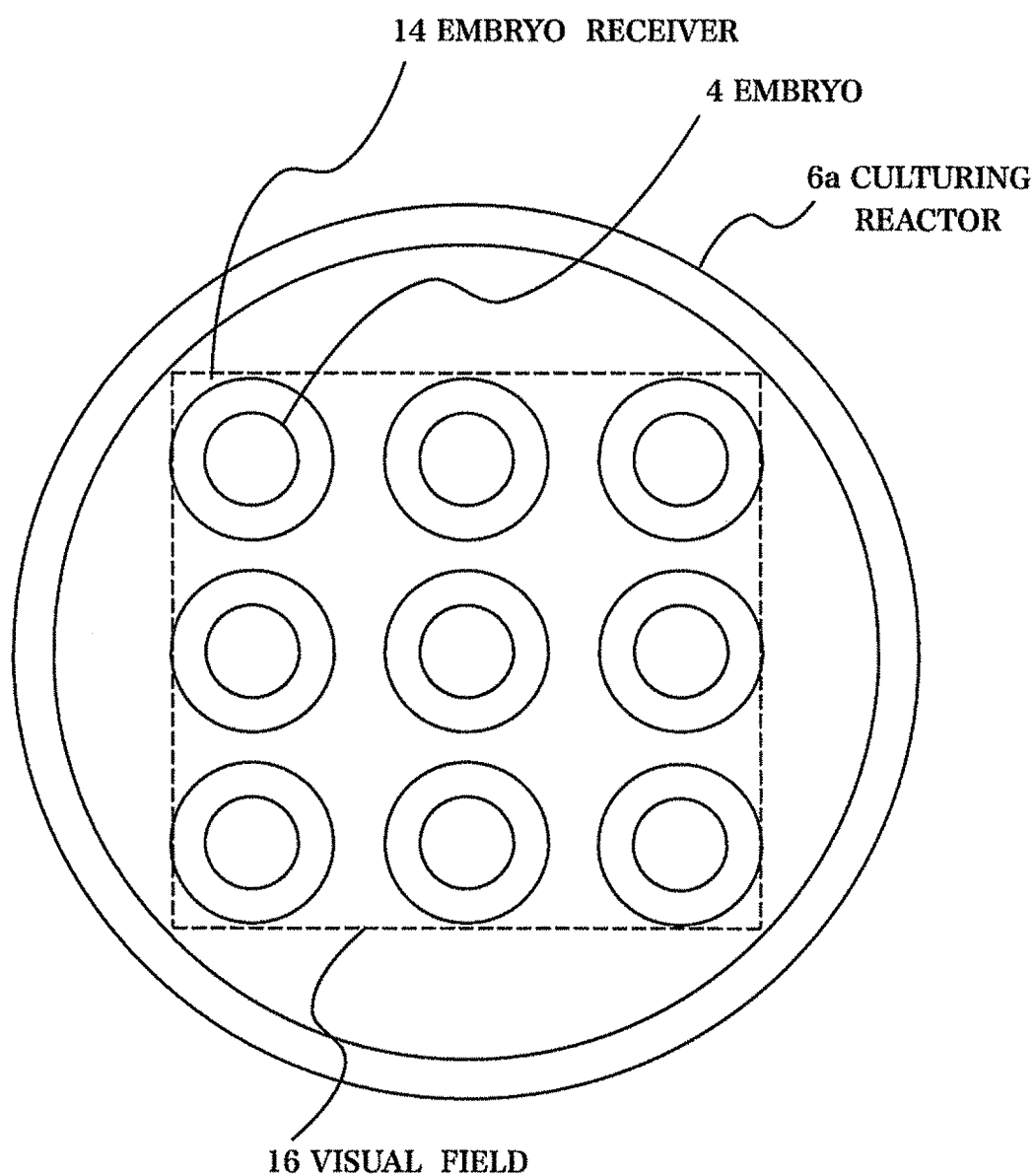
FIG. 20 is a schematic diagram showing a culturing reactor 6a viewed in a vertical direction (Z direction)

FIG. 20 is a schematic diagram showing the culturing reactor 6a when viewed in the vertical direction (Z direction). FIG. 20 shows a state that the embryos 4 are arranged in the embryo receivers 14. The inside of a dashed line represents a visual field 16 as an image pickup range of the camera unit 9 (image pickup unit).

FIGS. 21A and 21B are diagrams showing the image processing according to the first embodiment. FIG. 21A is a schematic diagram of a part of time-series image obtained by picking up an image of the culturing reactor 6a when the part concerned is subjected to the threshold-value processing of S103 of FIG. 4. FIG. 21B is a schematic diagram when the plugging processing of S104 of FIG. 4 is executed.

It is assumed that the embryo quality evaluation assistance apparatus 3a executes the processing of FIG. 4. A shadow of the embryo receiver 14 is contained in the time-series image obtained by picking up the image of the culturing reactor 6a, and thus a shadow area 15 of the embryo receiver 14 is extracted through the threshold-value processing of S103 as shown in FIG. 21A. Furthermore, through the plugging processing of S104, the shadow area 15 and the area in the neighborhood of the circumference of the embryo 4 are coupled to each other as shown in FIG. 21B, and thus they are not discriminated from each other. Therefore, the embryo image cannot be accurately extracted. Therefore, in the second embodiment, the embryo quality evaluation assistance apparatus 3a executes the processing shown in FIG. 22 to extract the embryo image.

Figure 22:
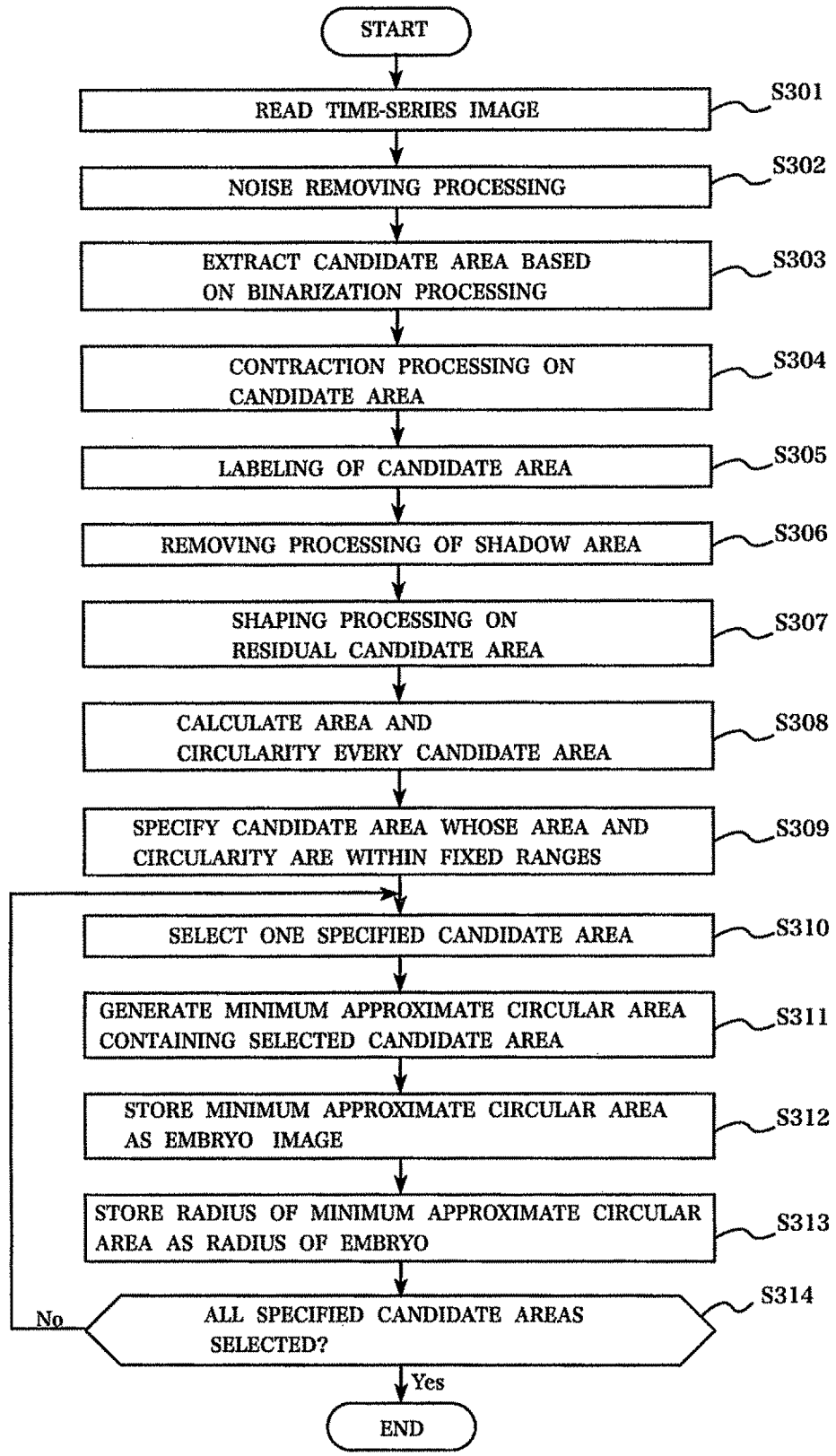
FIG. 22 is a flowchart showing extraction processing of an embryo image in a second embodiment.

FIG. 22 is a flowchart of the extraction processing of the embryo image in the second embodiment.

The controller 21 of the embryo quality evaluation assistance apparatus 3a reads a time-series image stored in the storage unit 22 into RAM (S301). Subsequently, the controller 21 subjects the time-series image read in S301 to noise removing processing (S302).

Subsequently, the controller 21 extracts a candidate area through the binarization processing (S303).

As described above, the shadow area 15 and the area in the neighborhood of the circumference have nearly equal gradation values, and thus the candidate area cannot be extracted with the shadow area 15 excluded. Therefore, the threshold value of the binarization processing in S303 is set to such a value that all the areas in the neighborhood of the circumference of the embryo 4 can be extracted as candidates.

For example, when the time-series image is a grayscale image whose pixel values have gradation values from 0 to 255, the pixel value "0" is set to the darkest gradation, and the pixel value "255" is set to the lightest (brightest) gradation. Furthermore, the threshold value of the binarization processing is set to a value larger than the gradation values of the pixels contained in the area in the neighborhood of the circumference of the embryo 4. The controller 21 extracts a pixel having a gradation value smaller than the threshold value as a candidate area. The controller 21 sets the pixel value "1" to a pixel extracted as a candidate area, and sets the pixel value "0" to a pixel which is not extracted as a candidate area.

Subsequently, the controller 21 executes the contraction processing on the candidate area extracted in S303 at a fixed number of times (S304). The candidate area extracted through the processing of S303 contains a shadow area 15, and there is a case where no clear boundary exists between the shadow area 15 and the area in the neighborhood of the circumference of the embryo 4 at the time point when the processing of S303 is finished. However, pixels having the pixel value "0" sprinkle between the shadow area 15 and the area in the neighborhood of the circumference of the embryo 4. Accordingly, the controller 21 repeats the contraction processing of S304, whereby the area of the pixel value "0" between the shadow area 15 and the area in the neighborhood of the circumference of the embryo 4 expands so as to surround the embryo 4. Accordingly, the boundary line between the shadow area 15 and the area in the neighborhood of the circumference of the embryo 4 is clear.

Subsequently, the labeling of candidate areas is executed (S305). The controller 21 allocates the same number to each set of linked candidate area pixels, thereby labeling each candidate area. The set of the linked candidate area pixels is the set of pixels which have the pixel value "1" of the candidate area and are positionally adjacent to one another.

The candidate areas which are discriminated from one another by labeling contain an area of plural embryos 4, plural shadow areas 15, a noise area such as dust, oose or the like, etc.

Subsequently, the controller 21 executes the removing processing of the shadow area 15 (S306). In the removing processing of the shadow area 15, the controller 21 calculates the area of each labeled candidate area and the size of the rectangle surrounding the labeled candidate area every labeled candidate area. Then, the controller 21 removes the shadow area 15 on the basis of the calculated area and the size of the rectangle.

Figure 23:
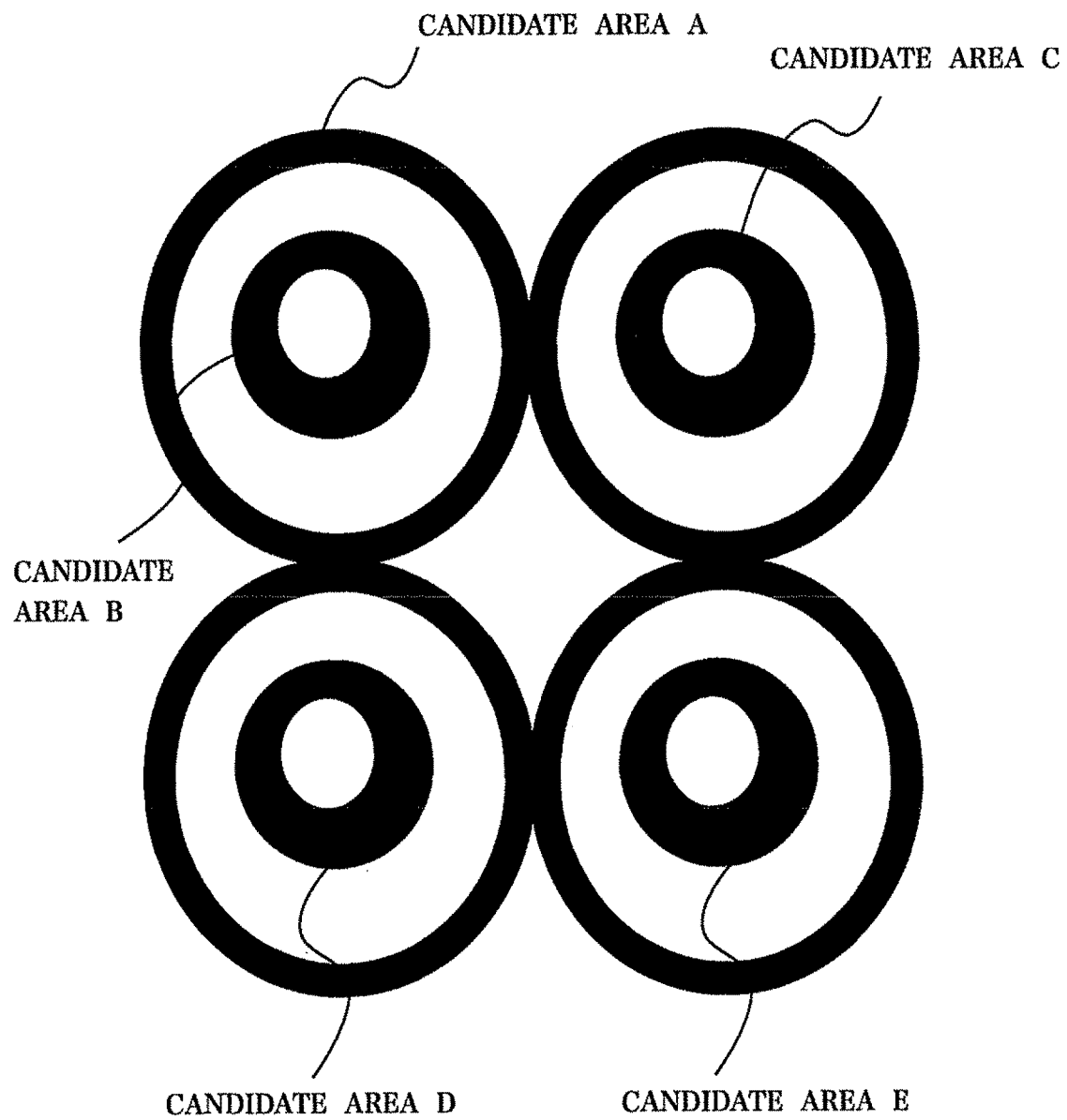
FIG. 23 is a diagram showing an image in which plural shadow areas 15 are linked to one another.

FIG. 23 is a diagram showing an image in which plural shadow areas 15 are linked to one another. In FIG. 23, a candidate area A represents an area where the plural shadow areas 15 are linked to one another, and candidate areas B to E represent areas of the embryos 4

When the distance between the embryo receivers 4 is not sufficient or when burr occurring when the embryo receivers 14 are processed exist, the plural shadow areas 15 may be linked to one another. In such a case, the area of the candidate area A is a larger value as compared with the areas of the candidate areas B to E. Therefore, the controller 21 removes a candidate area having a large area (the candidate area A in the example of FIG. 23) as the shadow area 15.

Figure 24:
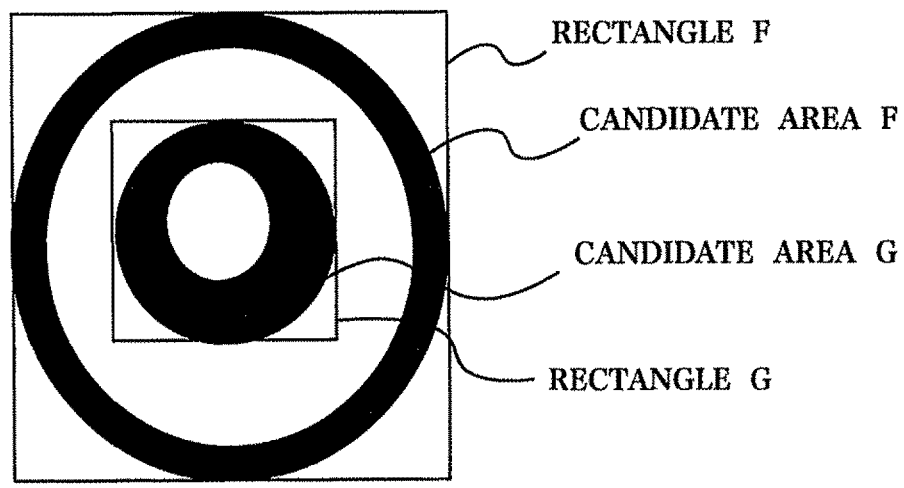
FIG. 24 is a diagram showing rectangles surrounding candidate areas.

FIG. 24 is a diagram showing rectangles surrounding candidate areas. A rectangle F surrounds the candidate area F corresponding to the shadow area 15, and a rectangle G surrounds a candidate area G corresponding to the area of an embryo 4.

The occupation area of the area of the embryo 4 in the image is known, and thus the controller 21 can remove the shadow area 15 on the basis of the area of the rectangle surrounding the candidate area. For example, when the area of the rectangle surrounding the candidate area is larger than a size which the embryo 4 can have during the culturing period, the controller 21 removes the candidate area concerned as the shadow area 15. Furthermore, when the area of the rectangle surrounding the candidate area is within a size range which the embryo 4 can have during the culturing period, the controller 21 does not remove the candidate concerned. In the example of FIG. 24, the controller 21 removes the candidate area F as the shadow area 15, and the controller 21 does not remove the candidate area G.

Figure 25:
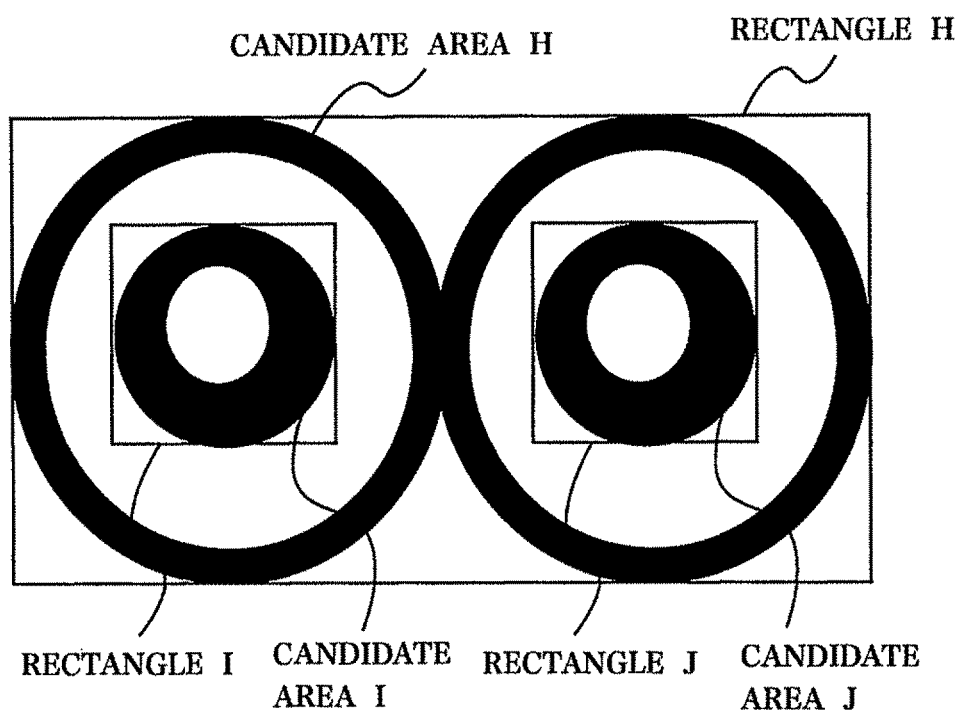
FIG. 25 is a diagram showing a rectangle surrounding candidate areas in which the plural shadow areas 15 are linked to one another.
Figure 27:
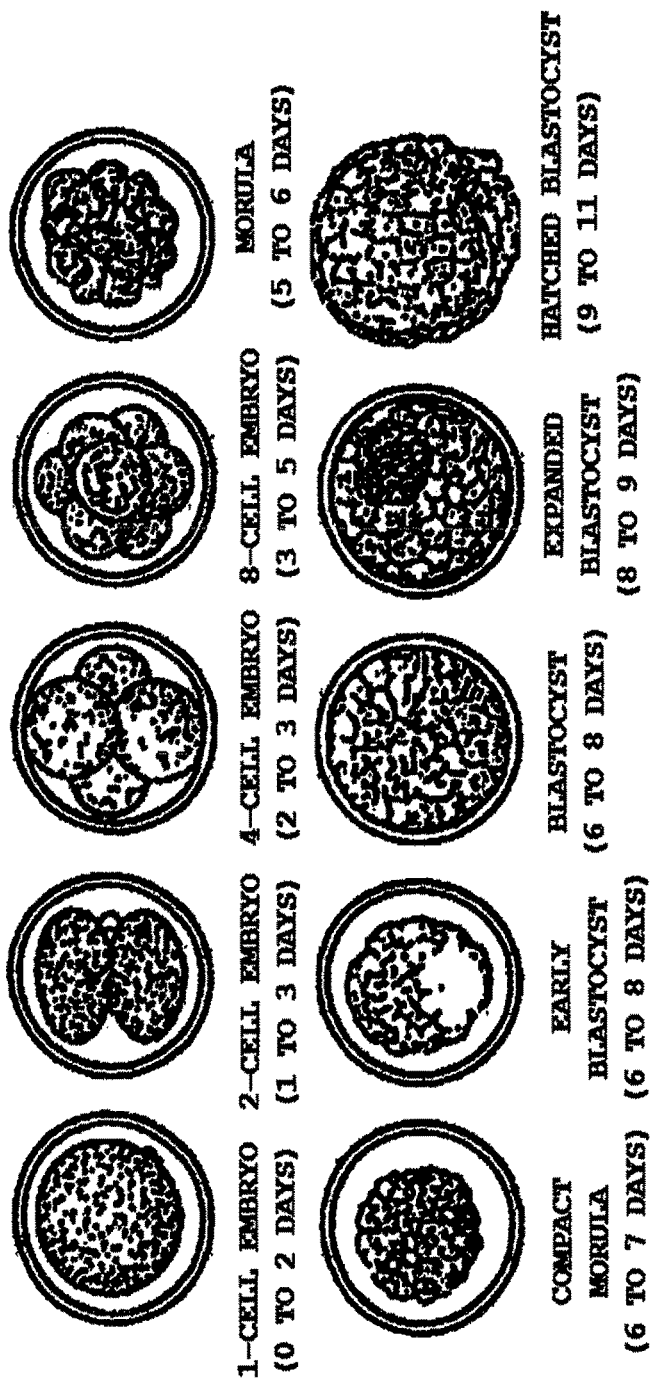
FIG. 27 is a diagram showing elapsed days after fertilization and growth stages of embryos (embryos of cattle).

FIG. 25 is a diagram showing a rectangle surrounding a candidate area in which plural shadow areas 15 are linked to one another. A rectangle H surrounds a candidate area H in which plural shadow areas 15 are linked to one another, and rectangles T and J surround candidate areas I and J corresponding to the areas of embryos 4, respectively.

The controller 21 can calculate circularity from the aspect ratio of the rectangle and remove the shadow area 15 on the basis of the calculated circularity. For example, when the calculated circularity is lower than a predetermined value, the controller 21 removes the area concerned as the shadow area 15. Furthermore, when the calculated circularity is higher than a predetermined value, the controller 21 does not remove the area concerned. In the example of FIG. 25, the candidate area H is removed as the shadow are 15, and the candidate areas I and J are not removed.

Subsequently, the controller 21 executes shaping processing on the residual candidate areas (S307). In the shaping processing, the controller 21 executes expansion processing on the residual candidate areas at a predetermined frequency. The frequency of the expansion processing is set to such a value that the candidate areas discriminated by the labeling of S305 are not linked to one another. Furthermore, the controller 21 executes the plugging processing on the residual candidate areas.

Subsequently, the controller 21 calculates the area and the circularity every candidate area (S308). The calculation processing of the area and the circularity is the same as the first embodiment.

Subsequently, the controller 21 specifies as the area of the embryo 4 a candidate area whose area and circularity are respectively within fixed ranges (S309). For example, a candidate area whose area is smaller than a fixed value is regarded as a noise area such as dust, oose or the like and removed, and further a candidate area whose circularity is within a fixed range is specified as the area of the embryo 4.

For example, a user may input the number of embryos 4 arranged in the culturing reactor 6a through the input unit 25, thereby specifying the number of candidate areas to be specified as the areas of embryos 4.

Subsequently, the controller 21 selects one of the specified candidate areas (S310), and generates the minimum approximate circular area containing the selected candidate area (S311). The processing of generating the minimum approximate circular area is the same as the first embodiment.

Subsequently, the controller 21 cuts out and stores the minimum approximate circular area as an embryo image (S312). Furthermore, the controller 21 stores the radius of the minimum approximate circular area as the radius of the embryo (S313).

Subsequently, the controller 21 checks whether all the specified candidate areas have been already selected or not (S314).

When there is any non-selected candidate area, the controller 21 repeats the processing from S310. When all the candidate areas have been selected, the controller 21 finishes the processing.

As described above, according to the second embodiment, the time-series images are picked up while the plural embryos arranged in the plural embryo receivers 14 are visually set within a visual field, and the plural embryo images are cut out from the time-series images.

The embryos 4 are arranged in the embryo receivers 14, and thus the positional relationship between the embryos 4 is not varied. Accordingly, even when the plural embryos 4 are arranged in the culturing reactor 6a, the embryos 4 can be observed without mixing up the embryos 4.

Furthermore, the embryo quality evaluation assistance apparatus 3a removes the shadow area caused by the embryo receiver 14, so that the embryo image can be accurately cut out.

Third Embodiment

Next, a third embodiment according to the present invention will be described. In the third embodiment, the quality of the embryo is determined on the basis of the calculated feature amount.

The same elements as described with respect to the first embodiment are represented by the same reference numerals, and the description thereof is omitted.

A normal embryo repeats cell division at plural times within a fixed time. Therefore, the feature amount analyzing unit 35 of the third embodiment calculates a peak occurrence frequency concerning the area of an active site within a fixed time, and uses the calculated peak occurrence frequency for the quality determination processing of the embryo. The peak occurrence frequency of the area of the active site corresponds to the occurrence frequency of the cell division.

The peak occurrence frequency of the area of the active site is set to a frequency at which the increment of the area of the active site exceeds a predetermined threshold value in the time-series data of the area of the active site, for example.

Referring to FIG. 17, in the case of a normal embryo, the area of the active site increases to 2000 $\mu m^2$ or more just before the growth stage of the expanded blastocyst, and then keeps 2000 $\mu m^2$ or more. On the other hand, referring to FIG. 18, in the case of a degenerated embryo, the area of the active site does not exceed 2000 $\mu m^2$ or more after the growth stage of 4-cell cleavage. On the basis of this knowledge, the feature amount analyzing unit 35 of the third embodiment calculates an accumulation time Lt for which the area of the active site keeps a value smaller than a predetermined threshold value from the time when the embryo reaches a predetermined growth stage, and uses the calculated accumulation time Lt for the quality determination processing of the embryo. Here, the time when the embryo reaches the predetermined growth stage contains the time when observation of the embryo is started.

Next, an example of the quality determination processing of the embryo will be described.

In the quality determination processing of the embryo, the peak occurrence frequency of the area of the active site (=the occurrence frequency of cell division) within a fixed time is set as a first determination condition. Furthermore, Lt is set as a second determination condition.

Specifically, the controller 21 of the embryo quality evaluation assistance apparatus 3 sets Q1 to 1 when the occurrence frequency of the cell division is equal to three times or more, sets Q1 to 0.5 when the occurrence frequency of the cell division is equal to once or twice, and also sets Q1 to zero when the occurrence frequency of the cell division is equal to zero. Furthermore, the controller 21 normalizes Lt so that Lt has a value from 0 to 1, and calculates Q2=max (0, (0.5−Lt)× 2). Here, x(a,b) represents a function taking larger one of values of a and b. For example, when Lt is equal to zero, Q2=1. When Lt is equal to 0.5 or more, Q2=0.

Lt is normalized so that the accumulation time from the time when the embryo reaches a predetermined growth stage is equal to 1. It can be said that the normalized Lt represents the probability that the embryo is degenerated.

The controller 21 calculates Q=Q1×Q2, and sets an evaluation rank of the embryo in accordance with the value of Q. The controller 21 sets a higher evaluation rank as the value of Q is larger.

As described above, the controller 21 determines the quality of the embryo in accordance with the peak occurrence frequency of the area of the active site and the accumulation time Lt for which the area of the active site keeps a value smaller than the predetermined threshold value.

However, the quality determination processing of the embryo described above is an example, and the quality of the embryo may be determined by using another feature amount. For example, as in the case of the first embodiment, the arrival time to each growth stage, the occurrence time, frequency and recovery time of rapture, etc. may be calculated and used for the quality determination processing of the embryo. Furthermore, the time variation of the average in brightness of pixels contained in the area of the embryo, the time variation of the standard deviation of brightness or the like may be calculated and used for the quality determination processing of the embryo.

As described above, according to the third embodiment, the embryo quality evaluation assistance apparatus 3 determines the quality of the embryo from the plural calculated feature amounts, and sets the evaluation rank for the embryo. Accordingly, the evaluation rank can be automatically set. Therefore, even during culture, stop of observation, stop of culture or the like of an embryo having a low evaluation rank can be determined, and thus the work can be performed more efficiently.

As described above, the preferred embodiments of the embryo quality evaluation assistance system, etc. according to the present invention have been described above, however, the present invention is not limited to these embodiments. It is apparent that persons skilled in the art can make various modifications or alterations to these embodiments within the scope of the technical idea disclosed in this specification, and it is understood that they belong to the technical scope of the present invention.

What is claimed is:

1. An embryo quality evaluation assistance system for assisting quality evaluation of an embryo, comprising:
    an embryo observing apparatus having an image pickup unit that picks up images of the embryo; and
    a computer that transmits and receives data to and from the embryo observing apparatus, wherein the computer comprises:
        a time-series image storing unit that stores time-series images picked up by the embryo observing apparatus;
        an embryo image extracting unit that extracts an embryo image from the time-series image; and
        an active site extracting unit that compares an embryo image based on a first time-series image with an embryo image based on a second time-series image picked up before or after a predetermined time from a pickup time of the first time-series image, and extracts as an active site a set of pixels associated with corresponding pixels of the first and second time-series images when a difference between pixel values of the corresponding pixels is larger than a predetermined threshold value, wherein
    the image pickup unit picks up the time-series images while the embryo is visually contained in a visual field; and
    the embryo image extracting unit extracts candidate areas through binarization processing, executes labeling of the candidate areas by allocating a same identifying number to each set of linked candidate area pixels, calculates an area of each labeled candidate area and a size of a rectangle surrounding each labeled candidate area, and removes the labeled candidate area when an area of the rectangle surrounding the labeled candidate area is larger than a size that the embryo can have during a culturing period or when a circularity calculated from an aspect ratio of the rectangle is lower than a predetermined value.

2. The embryo quality evaluation assistance system according to claim 1, wherein the active site extracting unit corrects rotation of the embryo to extract an active site.

3. The embryo quality evaluation assistance system according to claim 1, wherein the computer further comprises a processing result display unit that displays the active site extracted by the active site extracting unit while discriminating the active site from other areas.

4. The embryo quality evaluation assistance system according to claim 1, wherein the computer further comprises a feature amount calculating unit that calculates a size of the embryo from the embryo image extracted by the embryo image extracting unit and an area of the active site extracted by the active site extracting unit, as a feature amount of the embryo.

5. The embryo quality evaluation assistance system according to claim 4, wherein the computer further comprises a feature amount analyzing unit that specifies an arrival time to respective growth stages on the basis of a variation amount of the area of the active site calculated by the feature amount calculating unit, and specifies at least one of an occurrence time of raptures, an occurrence frequency of raptures or a recovery time from raptures on the basis of a variation amount of the size of the embryo calculated by the feature amount calculating unit.

6. The embryo quality evaluation assistance system according to claim 1, wherein the embryo observing apparatus picks up plural Z slice images as the time-series images every image pickup time, and the active site extracting unit compares an embryo image based on a first Z slice image with a fertilized image based on a second Z slice image which is picked up at a same Z position as the first Z slice image before or after a predetermined time from a pickup time of the first Z slice image, thereby extracting active sites at all Z positions.

7. The embryo quality evaluation assistance system according to claim 1, wherein the embryo observing apparatus further comprises a culturing container having plural embryo receivers formed therein, the image pickup unit picks up the time-series images while plural embryos arranged in the culturing container are visually contained in the visual field, and the embryo image extracting unit extracts plural embryo images from the time-series image.

8. The embryo quality evaluation assistance system according to claim 7, wherein the embryo image extracting unit removes a shadow area caused by the embryo receivers to extract the embryo images.

9. The embryo quality evaluation assistance system according to claim 5, wherein the feature amount analyzing unit determines quality of the embryo on the basis of the feature amount of the embryo calculated by the feature amount calculating unit.

10. The embryo quality evaluation assistance system according to claim 9, wherein the feature amount analyzing unit determines the quality of the embryo on the basis of a peak occurrence frequency of the area of the active site and an accumulation time for which the area of the active site keeps a value smaller than a predetermined threshold value.

11. An embryo quality evaluation assistance apparatus for transmitting and receiving data to and from an embryo observing apparatus having an image pickup unit that picks up an image of an embryo and assists quality evaluation of the embryo, comprising:
   a time-series image storing unit that stores a time-series image picked up by the embryo observing apparatus;
   an embryo image extracting unit that extracts an embryo image from the time-series image; and
   an active site extracting unit that compares an embryo image based on a first time-series image with an embryo image based on a second time-series image picked up before or after a predetermined time from a pickup time of the first time-series image, and extracts as an active site a set of pixels associated with corresponding pixels of the first and second time-series images when a difference between pixel values of the corresponding pixels is larger than a predetermined threshold value, wherein
   the image pickup unit picks up the time-series images while the embryo is visually contained in a visual field; and
   the embryo image extracting unit extracts candidate areas through binarization processing, executes labeling of the candidate areas by allocating a same identifying number to each set of linked candidate area pixels, calculates an area of each labeled candidate area and a size of a rectangle surrounding each labeled candidate area, and removes the labeled candidate area when an area of the rectangle surrounding the labeled candidate area is larger than a size that the embryo can have during a culturing period or when a circularity calculated from an aspect ratio of the rectangle is lower than a predetermined value.

12. An embryo quality evaluation assistance method for assisting quality evaluation of an embryo by an embryo observing apparatus having an image pickup unit for picking up an image of the embryo and a computer for transmitting and receiving data to and from the embryo observing apparatus, the method comprising:
   (a) picking up a time-series image by the embryo observing apparatus;
   (b) extracting an embryo image from the time-series image by the computer; and
   (c) comparing an embryo image based on a first time-series image with an embryo image based on a second time-series image picked up before or after a predetermined time from a pickup time of the first time-series image, and extracting as an active site a set of pixels associated with corresponding pixels of the first and second time-series images when a difference between pixel values of the corresponding pixels is larger than a predetermined threshold value, by the computer, wherein
   in step (a), the time-series images are picked up while the embryo is visually contained in a visual field; and
   in step (b), candidate areas are extracted through binarization processing, labeling of the candidate areas is executed by allocating a same identifying number to each set of linked candidate area pixels, the areas of each labeled candidate area and a size of a rectangle surrounding each labeled candidate area are calculated, and the labeled candidate area is removed when the area of the rectangle surrounding the labeled candidate area is larger than a size that the embryo can have during a culturing period or when a circularity calculated from an aspect ratio of the rectangle is lower than a predetermined value.

* * * * *

UNITED STATES PATENT AND TRADEMARK OFFICE
CERTIFICATE OF CORRECTION

PATENT NO. : 8,515,143 B2
APPLICATION NO. : 12/654823
DATED : August 20, 2013
INVENTOR(S) : Yasuhito Oonishi et al.

It is certified that error appears in the above-identified patent and that said Letters Patent is hereby corrected as shown below:

Title Page, Item (73) second Assignee should read:

(73) Assignee: --National Livestock Breeding Center, Incorporated Administrative Agency--.

Signed and Sealed this
Twenty-ninth Day of October, 2013

Teresa Stanek Rea
*Deputy Director of the United States Patent and Trademark Office*